US008349559B2

(12) United States Patent
Wojchowski

(10) Patent No.: US 8,349,559 B2
(45) Date of Patent: Jan. 8, 2013

(54) SYSTEM AND METHOD FOR IDENTIFYING ERYTHROPOIETIN-RESPONSIVE GENES

(75) Inventor: Don Wojchowski, Cape Elizabeth, ME (US)

(73) Assignee: Maine Medical Center, Portland, ME (US)

( * ) Notice: Subject to any disclaimer, the term of this patent is extended or adjusted under 35 U.S.C. 154(b) by 11 days.

(21) Appl. No.: 12/693,167

(22) Filed: Jan. 25, 2010

(65) Prior Publication Data
US 2010/0124753 A1 May 20, 2010

Related U.S. Application Data

(62) Division of application No. 11/982,958, filed on Nov. 6, 2007.

(60) Provisional application No. 60/857,623, filed on Nov. 8, 2006.

(51) Int. Cl.
C12Q 1/68 (2006.01)
G01N 33/53 (2006.01)

(52) U.S. Cl. .......................................... 435/6.1; 435/7.1

(58) Field of Classification Search .................. None
See application file for complete search history.

(56) References Cited

U.S. PATENT DOCUMENTS

| 4,284,412 | A | 8/1981 | Hansen |
| 4,325,706 | A | 4/1982 | Gershman |
| 5,835,382 | A | 11/1998 | Wilson et al. |
| 5,888,774 | A | 3/1999 | Delcuve |
| 6,103,526 | A | 8/2000 | Smith et al. |
| 6,340,742 | B1 | 1/2002 | Burg et al. |
| 6,642,353 | B1 | 11/2003 | McConnell |
| 6,750,369 | B2 | 6/2004 | Connolly et al. |
| 6,998,124 | B1 | 2/2006 | Erickson-Miller et al. |
| 7,032,902 | B1 | 4/2006 | Olsson et al. |
| 7,084,245 | B2 | 8/2006 | Holmes et al. |
| 7,128,913 | B2 | 10/2006 | Burg et al. |

OTHER PUBLICATIONS

Gubin et al (Genomics, 1999. vol. 59, pp. 168-177).*
Baumann, R., and Dragon, S. 2005. Erythropoiesis and red cell function in vertebrate embryos. Eur J Clin Invest 35 Suppl 3:2-12.
Cantor, A.B., and Orkin, S.H. 2005. Coregulation of GATA factors by the Friend of GATA (FOG) family of multitype zinc finger proteins. Semin Cell Dev Biol 16:117-128.
Richmond T.D., Chohan M., and Barber, D.L. 2005. Turning cells red: signal transduction mediated by erythropoietin. Trends Cell Biol 15:146-155.
Koury, M.J., and Bondurant, M.C. 1990. Erythropoietin retards DNA breakdown and prevents programmed death in erythroid progenitor cells. Science 248:378-381.
Wu H., Liu, X., et al., 1995. Generation of committed erythroid BFU-E and CFU-E progenitors does not require erythropoietin or the erythropoietin receptor. Cell 83:59-67.

Socolovsky, M., et al., 1999. Fetal anemia and apoptosis of red cell progenitors in Stat5a-/-5b-/- mice: a direct role for Stat5 in Bcl-X(L) induction. Cell 98:181-191.
Ghaffari, S., et al., 2006. AKT induces erythroid-cell maturation of JAK2-deficient fetal liver progenitor cells and is required for Epo regulation of erythroid-cell differentiation. Blood 107:1888-1891.
Levine, A.J., et al., 2006. Coordination and communication between the p53 and IGF-1-AKT-TOR signal transduction pathways. Genes Dev 20:267-275.
Hammerman, P.S., et al., 2005. Pim and Akt oncogenes are independent regulators of hematopoietic cell growth and survival. Blood 105:4477-4483.
Maiese, K, Li, F., and Chong, Z.Z. 2005. New avenues of exploration for erythropoietin. Jama 293:90-95.
Scott, J., Phillips, GC., 2005, Erythropoietin in sports: a new look at an old problem. Curr Sports Med Rep. Aug;4 (4):224-226.
Sambrook, et al., Molecular Cloning, A Laboratory Manual, 2d ed., 1989.
Menon, M.P., et al., 2006. Signals for stress erythropoiesis are integrated via an erythropoietin receptor-phosphotyrosine-343-Stat5 axis. J Clin Invest 116:683-694.
Levine, A.J., and Brivanlou, A.H. 2006. GDF3 at the crossroads of TGF-beta signaling. Cell Cycle 5:1069-1073.
Tanaka, M., and Miyajima, A. 2003. Oncostatin M, a multifunctional cytokine. Rev Physiol Biochem Pharmacol 149:39-52.
Kucia, M., et al., 2005. Trafficking of normal stem cells and metastasis of cancer stem cells involve similar mechanisms: pivotal role of the SDF-1-CXCR4 axis. Stem Cells 23:879-894.
Scott, L.M., et al., 2003. Deletion of alpha4 integrins from adult hematopoietic cells reveals roles in homeostasis, regeneration, and homing. Mol Cell Biol 23:9349-9360.
Arroyo, A.G., et al., 1999. Alpha4 integrins regulate the proliferation/differentiation balance of multilineage hematopoietic progenitors in vivo. Immunity 11:555-566.
Barton Furness, S.G., and McNagny, K. 2006. Beyond mere markers: functions for CD34 family of sialomucins in hematopoiesis. Immunol Res 34:13-32.
Jorcyk, C.L., et al., 2006. Oncostatin M induces cell detachment and enhances the metastatic capacity of T-47D human breast carcinoma cells. Cytokine 33:323-336.
McPherron, A.C., and Lee, S.J. 1993. GDF-3 and GDF-9: two new members of the transforming growth factor-beta superfamily containing a novel pattern of cysteines. J Biol Chem 268:3444-3449.
Elisseeva, E.L., et al., 2000. NMR studies of active N-terminal peptides of stromal cell-derived factor-1. Structural basis for receptor binding. J Biol Chem 275:26799-26805.
Peterson, J.A., et al., 2005. Heparin II domain of fibronectin uses alpha4beta1 integrin to control focal adhesion and stress fiber formation, independent of syndecan-4. J Biol Chem 280:6915-6922.
Rose, D.M. 2006. The role of the alpha4 integrin-paxillin interaction in regulating leukocyte trafficking. Exp Mol Med 38:191-195.

(Continued)

Primary Examiner — Celine Qian
(74) Attorney, Agent, or Firm — Pierce Atwood LLP; Kevin M. Farrell; David J. Wilson

(57) ABSTRACT

The present invention relates to the generation of a population of Epo-responsive marrow derived cells that express Epo-responsive genes and gene products. The present invention also relates to the detection of Epo-responsive genes and gene products as well as to the detection of the administration of Epo, Epo-derivatives and Epo-mimetics in subjects.

8 Claims, 25 Drawing Sheets

OTHER PUBLICATIONS

Dekan, G., Gabel, C., and Farquhar, M.G. 1991. Sulfate contributes to the negative charge of podocalyxin, the major sialoglycoprotein of the glomerular filtration slits. Proc Natl Acad Sci U S A 88:5398-5402.

Doyonnas, R., et al., 2005. Podocalyxin is a CD34-related marker of murine hematopoietic stem cells and embryonic erythroid cells. Blood 105:4170-4178.

Wilson, A., and Trumpp, A. 2006. Bone-marrow haematopoietic-stem-cell niches. Nat Rev Immunol 6:93-106.

Nagasawa, T. 2006. Microenvironmental niches in the bone marrow required for B-cell development. Nat Rev Immunol 6:107-116.

Chasis, J.A. 2006. Erythroblastic islands: specialized microenvironmental niches for erythropoiesis. Curr Opin Hematol 13:137-141.

Lee, G., et al., 2006. Targeted gene deletion demonstrates that cell adhesion molecule ICAM-4 is critical for erythroblastic island formation. Blood, Sep. 15;108(6):2064-2071.

Zang, H., et al., 2001. The distal region and receptor tyrosines of the Epo receptor are non-essential for in vivo erythropoiesis. Embo J 20:3156-316.

Matsumoto, A., et al., 1997. CIS, a cytokine inducible SH2 protein, is a target of the JAK-STAT5 pathway and modulates STAT5 activation. Blood 89:3148-3154.

Tanaka, M., et al., 2003. Targeted disruption of oncostatin M receptor results in altered hematopoiesis. Blood 102:3154-3162.

Son, B.R., et al., 2006. Migration of bone marrow and cord blood mesenchymal stem cells in vitro is regulated by stromal-derived factor-1-CXCR4 and hepatocyte growth factor-c-met axes and involves matrix metalloproteinases. Stem Cells 24:1254-1264.

Menon, M.P., et al., 2006. Core erythropoietin receptor signals for late erythroblast development. Blood 107:2662-2672.

Sathyanarayana, P., et al., Erythropoietin Modulation of Podocalyxin and a Proposed Erythroblast Niche. Blood. Apr. 2007, vol. 110, pp. 509-518.

Gubin, et al., Genomics, 1999. vol. 59, pp. 168-177.

Karur, et al., Blood, 2006. vol. 108, pp. 1524-1532.

Sawada, et al., Journal of Clinical Investigation, 1989, vol. 83, pp. 1701-1709.

* cited by examiner

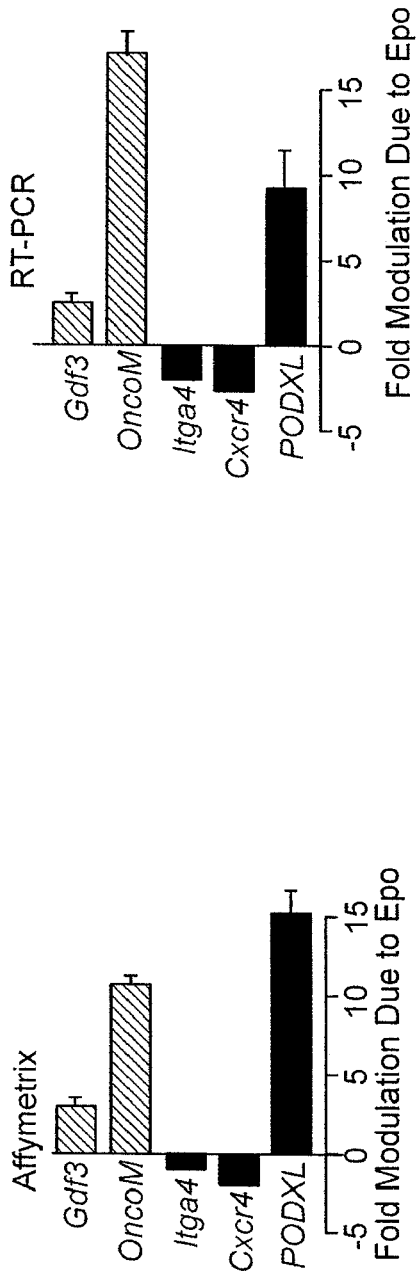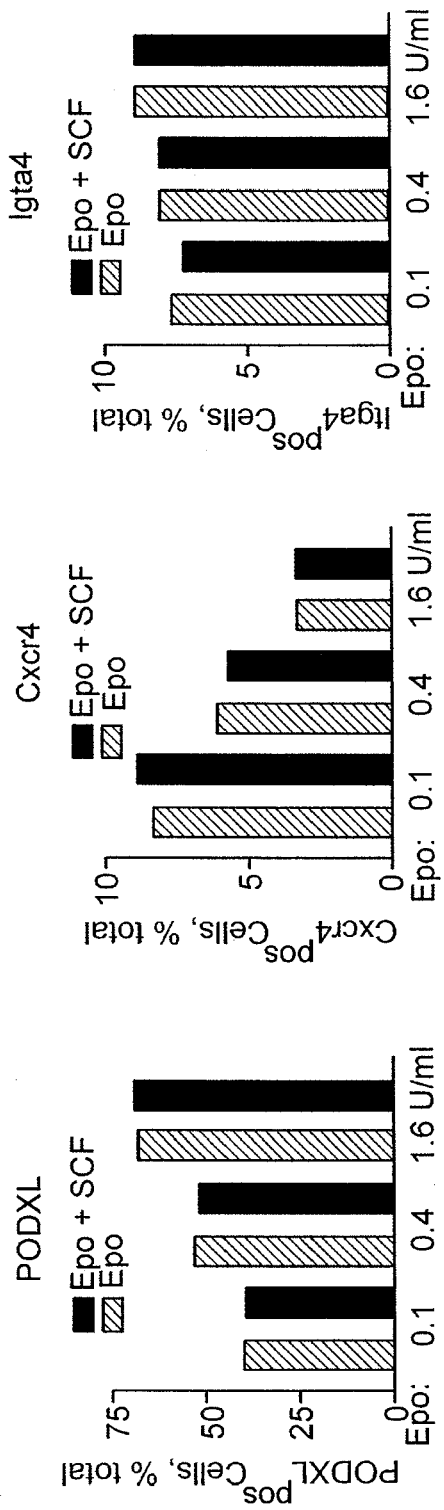
Figure 1D
Figure 1E
Figure 1F

BONE MARROW

SYSTEM AND METHOD FOR IDENTIFYING ERYTHROPOIETIN-RESPONSIVE GENES

This work was supported (in part) by NIH grants R01 HL044491, R01 DK059472 and NCRR-COBRE NIH grant R01 HL044491 and NCRR-COBRE NIH grant P20-RR18789. The government may have certain rights in this invention.

BACKGROUND OF THE INVENTION

To maintain tissue oxygenation, red cell formation from progenitors in bone marrow, spleen and fetal liver is strictly regulated (Baumann, R., and Dragon, S. 2005. Erythropoiesis and red cell function in vertebrate embryos. *Eur J Clin Invest* 35 Suppl 3:2-12). In early progenitors, erythroid lineage commitment is directed by a unique set of DNA binding and transcription factors (e.g., GATA-1, EKLF-1 and FOG-1) (Cantor, A. B., and Orkin, S. H. 2005. Coregulation of GATA factors by the Friend of GATA (FOG) family of multitype zinc finger proteins. *Semin Cell Dev Biol* 16:117-128). Subsequent pro-erythroblast expansion is likewise sharply controlled, in part, by the glycoprotein hormone erythropoietin (Epo) (Richmond, T. D., Chohan, M., and Barber, D. L. 2005. Turning cells red: signal transduction mediated by erythropoietin. *Trends Cell Biol* 15:146-155). Epo is expressed in adult kidney via hypoxia-inducible transcription factor pathways (Richmond, T. D., et al., 2005. Turning cells red: signal transduction mediated by erythropoietin. *Trends Cell Biol* 15:146-155). Epo's subsequent interactions with its single transmembrane receptor (EpoR) are then thought to selectively support erythroblast survival (Koury, M. J., and Bondurant, M. C. 1990. Erythropoietin retards DNA breakdown and prevents programmed death in erythroid progenitor cells. *Science* 248:378-381; Wu, H., Liu, X., et al., 1995. Generation of committed erythroid BFU-E and CFU-E progenitors does not require erythropoietin or the erythropoietin receptor. *Cell* 83:59-67; Socolovsky, M., et al., 1999. Fetal anemia and apoptosis of red cell progenitors in Stat5a−/−5b−/− mice: a direct role for Stat5 in Bcl-X(L) induction. *Cell* 98:181-191). Redundant EpoR-activated survival pathways, in fact, have been described that depend upon phosphoinositide-3 kinase (PI3 kinase) and AKT-dependent regulation of Foxo3a (Ghaffari, S., et al., 2006. AKT induces erythroid-cell maturation of JAK2-deficient fetal liver progenitor cells and is required for Epo regulation of erythroid-cell differentiation. *Blood* 107:1888-1891) and (m)TOR (Levine, A. J., et al., 2006. Coordination and communication between the p53 and IGF-1-AKT-TOR signal transduction pathways. *Genes Dev* 20:267-275), as well as EpoR/Jak2/Stat5-dependent induction of Pim1 kinase (Hammerman, P. S., et al., 2005. Pim and Akt oncogenes are independent regulators of hematopoietic cell growth and survival. *Blood* 105:4477-4483) and the Bcl2 orthologue Bcl-xl (Socolovsky, M., et al., 1999. *Cell* 98:181-191). These response pathways therefore likely contribute in important ways to Epo's clinical utility as an anti-anemia agent and as an apparent cytoprotective factor for injured heart, endothelial, neuronal and renal cells (Maiese, K., Li, F., and Chong, Z. Z. 2005. New avenues of exploration for erythropoietin. *Jama* 293:90-95). Currently, research into Epo-mediated physiological processes such is hindered by the lack of a substantially homogeneous population of bone marrow derived Epo-responsive cells. Such a population of cells would be a boon to Epo-research.

Epo has also been recognized as a performance supplement by certain athletes. It is thought to help the athlete as an ergogenic aid by eliminating fatigue symptoms by increasing red blood cell count thereby increasing stamina and performance. However, Epo also has potential detrimental side effects for the athlete and has been banned by most if not all sports organizations. Unfortunately, testing for Epo doping by prior art methods is difficult, time consuming and/or inaccurate and complicated by the fact that the body makes physiological amounts of Epo (Scott J, Phillips G C., 2005, Erythropoietin in sports: a new look at an old problem. Curr Sports Med Rep. August; 4 (4):224-6).

Thus, what is needed are new reagents and methods useful for the investigation of signaling pathways and cellular processes involving Epo as well as for an efficient and accurate in vivo/ex vivo methods suitable for the detection of physiologically active Epo, Epo derivatives and Epo mimetics in individuals.

SUMMARY OF THE INVENTION

The present invention relates to the generation of a novel population of Epo-responsive marrow derived cells that express Epo-responsive genes and gene products. Said novel population of Epo-responsive marrow derived cells are generated by isolating a subset of bone marrow cells that are, in one embodiment, $Kit^{pos}CD71^{high}$, then culturing the $Kit^{pos}CD71^{high}$ cells in the absence of Epo or in the absence of hematopoietic cytokines (including Epo) for a period of time sufficient to substantially decrease Epo receptor signaling and then exposing them to Epo for a period of time sufficient to permit the expression of Epo-responsive genes. The present invention also relates to the detection of Epo-responsive genes and gene products. Further, the present invention relates to the detection of the administration of Epo, Epo-derivatives and Epo-mimetics in subjects based on the detection of expression of Epo-responsive genes.

DESCRIPTION OF THE INVENTION

Figure 1A:
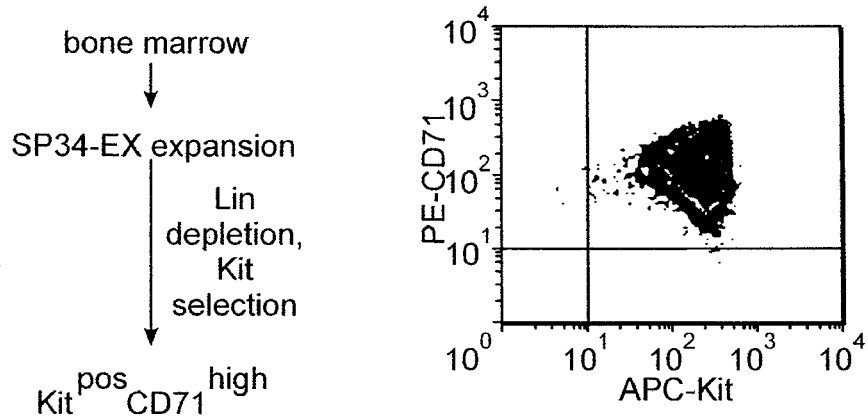
FIG. 1. Gene array-based discovery of Epo-modulated cytokines and cell surface adhesion factors in murine bone marrow derived erythroblasts. A) Illustrated are steps used to expand and isolate $Kit^{pos}CD71^{high}Ter119^{neg}$ erythroblasts, together with a representative flow cytometric profile. B) For erythroblasts prepared from n=4 independent bone marrow preparations, hematopoietic cytokines were withdrawn for 6 hours, and cells then were exposed to Epo (+/−5 U/mL). At 90 minutes, RNA was prepared and used in transcriptome analyses. As a control, levels of Epo-induced Cis1 transcript levels (right panel) were analyzed by RT-PCR. C) For Epo-regulated genes, genome-wide outcomes are illustrated by relative difference analyses. D) Affymetrix 430-2.0 array based analyses of Epo-regulated cytokine and cell surface adhesion factors. Values are mean fold-modulation by Epo (+/−SE, n=4). E) Quantitative RT-PCR analyses of Epo regulation of Onco-M, Gdf3, Cxcr4, Itga4 and PODXL. Values are means (+/−SE) and are normalized to beta-actin. F) For PODXL, Cxcr4, and Itga4, cell surface levels also were assayed (by flow cytometry) among $Kit^{pos}CD71^{high}$ erythroblasts following their isolation, and subsequent 24-hour culture in Epo at 0.1, 0.4 and 1.6 U/mL.

The present invention relates to the generation of a substantially homogeneous population of primary erythroblast cells (a population) which, following Epo-deprived and, in another embodiment, Epo- and hematopoietic cytokine-deprivation culture for a period of time sufficient to substantially decrease Epo receptor signaling, responds to the presence of Epo by modulating the transcription of various Epo-responsive genes including, for example, the up-regulation of podocalyxin (PODXL), oncostatin-M (Onco-M) and growth differentiation factor-3 (Gdf-3) as well as to the down-regulation of, for example, chemokine receptor-4 (Cxcr-4) and integrin alpha-4 (Itga-4). Although the present invention is not limited by any particular method for the generation of said cells, said cells may be generated by, for example, the techniques of the Exemplification section or by other methods as described herein.

In one embodiment, the substantially homogeneous population of primary erythroblast cells is Kit$^{pos}$CD71$^{high}$ when examined for these markers on the cell surface by, for example, flow cytometry. In another embodiment, the substantially homogeneous population of primary erythroblasts are also Ter119$^{neg}$ when examined by, for example, flow cytometry.

Such detection of cell surface markers is typically performed by immunofluorescent techniques such as flow cytometry. A flow cytometer is also known in the art as a fluorescence-activated cell-sorter (FACS). Flow cytometry is well known in the art for the detection and quantification of cell surface markers (e.g., antigens) such as proteins and, to a lesser extent, lipids and carbohydrates. (See, for example, U.S. Pat. No. 4,284,412 to Hansen and U.S. Pat. No. 4,325,706 to Gershman, both of which are incorporated herein by reference). Flow cytometry can be performed on both living and fixed or preserved cells, depending on the application. Flow cytometry can also be used to detect proteins and other molecules located within the cell. In such instances the cells are permeabilized either transiently (such as, for example, with live cells) or permanently (such as, for example, with cells that are being fixed or preserved).

Flow cytometry is performed by labeling target molecules with fluorescently labeled agents specific for the target. Usually, fluorescently labeled antibodies are used because of their specificity and selectivity for target molecules. The target cells are then analyzed by passing them through a beam of light of the appropriate wave length(s) for the excitation of the fluorescent tag. Multiple labels may be used of different colors allowing for the detection of several targets at one time. In this manner, several thousand cells per minute can be examined and the data plotted on scatter graphs and the like (e.g., see, FIG. 1A).

One example of the culture conditions of the present invention are as detailed in the Exemplification section of this specification although other culture conditions are also contemplated. In a preferred embodiment, bone marrow erythroblasts are isolated from a donor and cultured in for about 3½ days in a serum-free culture system (see, Exemplification section). In other embodiments, the period of time in which the bone marrow erythroblasts are cultured may vary from a period of about 2 days to 5 days. $Kit^{pos}CD71^{high}Ter117^{neg}$ cells were isolated and then cultured for about 6 hours in the absence of hematopoietic cytokines (including Epo) then stimulated with Epo for about 90 minutes. One practiced in the art will realize that variations of this procedure will also provide for the generation of the Epo-responsive genes of this invention. For example, cells may be cultured for lengths of time that differ than 90 minutes. Shorter or longer times will also provide for the generation and/or identification of other Epo-responsive genes. In one embodiment, the culture time that is suitable for the generation of Epo-responsive genes is between about 30 minutes and 24 hours. In another embodiment the culture time is between 45 minutes and 6 hours. In yet another embodiment, the culture time is between 1 hour and 3 hours.

One practiced in the art will also realize that the amount of Epo used to stimulate the expression of Epo-responsive genes may very. For example, the level of Epo used may vary depending upon the length of time in which the cells are in culture. Cells in culture for longer periods of time may require a lower concentration of Epo to initiate the transcription of the Epo-responsive genes. Likewise, higher concentrations may permit the quicker expression of the Epo-responsive genes. One practiced in the art will be able to determine ideal culture times in relation to Epo concentration by running dose response curves for differing periods of time, as is known in the art. In a preferred embodiment, the concentration of Epo used is between about 0.05 U/ml to about 100 U/ml. In a more preferred embodiment, the concentration of Epo used is between about 0.5 U/ml and 50 U/ml and in a more preferred embodiment, the concentration of Epo used in between about 1.0 U/ml and 10.0 U/ml.

One practiced in the art will also realize that cells designated as $Kit^{pos}CD71^{high}Ter117^{neg}$ will have cells that have a range of expression of the labeled markers. For example, cells that are $Kit^{pos}$ or $CD71^{high}$ may have expression levels of Kit ranging over two powers (e.g., fluorescent intensities ranging from $10^1$ to $10^3$ when analyzed by flow cytometry; also see FIG. 1A) and that $Kit^{neg}$, $CD71^{low}$ and $Ter117^{neg}$ cells may have expression of the marker molecule albeit at very limited levels.

The Epo-responsive cells of the present invention are characterized by the modulation of expression of Epo-responsive genes. In the present invention over 200 Epo-responsive genes were identified with high statistical significance. For several genes, the expression was modulated by two-fold or more by Epo. The modulated genes corresponded to cell surface or secreted factors. Two secreted cytokines identified in the present invention were Gdf-3 and Onco-M. Three cell surface adhesion/migration factors identified by the present invention were Cxcr-4, Ltga-4 and PODXL. In a preferred embodiment, the Epo-responsive genes of the present invention are recognized by the up-regulation of the transcription of PODXL, Onco-M and Gdf-3 and by the down-regulation of the Epo-responsive genes Cxxr-4 and Ltga-4. In a more preferred embodiment, PODXL is up-regulated by three-fold or more, Onco-M is up-regulated by three-fold or more and Gdf-3 is up-regulated by at least 50%. Additionally, in one embodiment, the Epo-responsive genes Cxcr-4 and Ltga-4 are down-regulated by at least two-fold (see, FIGS. 1D and 1E).

The up- and down-regulation of Epo-responsive genes may be detected by any methods known in the art used to detect changes in gene expression. Examples are PCR, RT-PCR, Southern blotting, Northern blotting, Western blotting, immunodetection (e.g., immunoflourescence, immuno-sandwich assays such as ELISA and immunodiffusion assays such as Ouchterlony) and electrophoresis (e.g., agarose, SDS-PAGE and 2D SDS-PAGE). All of these techniques are known to those practiced in the art (for example, see, Sambrook, et al., Molecular Cloning, A Laboratory Manual, 2d ed., 1989, incorporated herein by reference). As can be seen from the exemplified list of techniques, Epo-responsive genes can be detected at the level of transcription, translation or at the protein level. One skilled in the art is able to choose the method or methods best suited for the gene being studied.

The present invention also is directed towards a method for the detection or identification of Epo-responsive genes, the method comprising providing a substantially homogeneous primary erythroblast population from bone marrow which, following Epo-deprivation culture for a period of time sufficient to substantially decrease Epo receptor signaling, responds to culture in the presence of Epo by up-regulating podocalyxin transcription by more than 3-fold. In one embodiment, the substantially homogeneous population of erythroblasts are selected and cultured as described above and in the Exemplification section that follows. Likewise, the concentration of Epo used and the period of time that it is used to generate Epo-responsive genes is as described above and in the Exemplification section below.

The culture system used in which the serum-free media is substantially free of Epo may also comprise, in one embodiment, insulin in a range from about 10 ng/ml up to about 50 ng/ml. Said serum-free medium may also comprise transferrin at a concentration of about 1.0 µg/ml to about 1000 µg/ml. In a preferred embodiment, said transferrin is between about 5.0 µg/ml and 500 µg/ml. In a more preferred embodiment, the transferrin is provided at a level of about 100 µg/ml. Said serum-free culture medium may also comprise bovine serum albumin (BSA) at a concentration (w/v) of between about 0.05% and 10.0%. In a more preferred embodiment, said BSA may be between about 0.1% and 5.0% and in a most preferred embodiment between about 0.04% and 1.0%. Said medium that is substantially free of Epo need not be serum-free but may contain serum if said serum is substantially free of Epo.

Once said cells are cultured in the medium which is substantially free of Epo for a time sufficient to substantially decrease Epo receptor signaling (as described above and in the Exemplification section below) of, in one embodiment, of about 3.5 days, the cells are then cultured in the presence of Epo at levels sufficient to modulate transcription of Epo-responsive genes. Examples of the levels of Epo necessary and the length of culture necessary for the modulation of Epo-responsive genes are described above and below in the Exemplification section.

Epo-responsive genes may be identified by any method known to those practiced in the art including PCR, RT-PCR, electrophoresis (e.g., agarose and SDS-PAGE, 2-D electrophoresis), immunological assays, Southern and Northern blotting, etc. In a preferred embodiment, said assays are compared to cells cultured in substantially identical conditions but without the addition of Epo so that Epo-responsive genes can be identified with greater ease.

The present invention also relates to methods of detecting the effects of exogenous Epo or derivatives or mimetics thereof, the method comprising testing a blood sample from an individual, determining the level of expression of an Epo-responsive gene or gene product on, for example, the surface of circulating erythroid cells in the blood sample of the individual and comparing the level of expression of the Epo-responsive gene with a standard level of expression accepted as representative of the in vivo expression level on the surface of the red blood cells in the individual in the absence of exogenous Epo or derivatives or mimetics thereof, a substantial increase in the level of the Epo-responsive gene as compared with the standard level of expression accepted as representative of the in vivo expression level on the surface of red blood cells in the individual in the absence of exogenous Epo or derivatives or mimetics thereof, being indicative of the effects of exogenous Epo or derivatives or mimetics thereof.

The present invention is not limited to any particular Epo derivatives or mimetics providing the Epo derivative or mimetic is capable of modulating Epo-responsive genes in vivo. This is because the methods of the present invention are not limited by the agent that modulates the Epo-responsive gene since the methods of the present invention are directed towards the detection of the gene transcription product either directly (e.g., RNA) or after further down line processing (e.g., proteins). Epo derivatives and mimetics are well known in the art. Some non-limiting examples include Aransep® (Amgen, Thousand Oaks, Calif.), Epo-PEG conjugates (U.S. Pat. No. 6,340,742 to Burg, et al., issued Jan. 22, 2002 and incorporated herein by reference). Other examples of erythropoietin mimetics are those identified by, for example, the methods of U.S. Pat. No. 5,835,382, issued to Wilson, et al., on Nov. 10, 1998; U.S. Pat. No. 7,048,245 issued to Holmes, et al., on Aug. 1, 2006; U.S. Pat. No. 7,032,902 issued to Olsson, et al., on May 2, 2006; U.S. Pat. No. 6,750,369 issued to Connolly, et al., on Jun. 15, 2004 and U.S. Pat. No. 6,642,353 issued to McConnell on Nov. 4, 2003, all of which are incorporated herein by reference, are contemplated as identified by the methods of the present invention for their ability to modulate Epo-responsive genes in vivo. Additionally, erythropoietin conjugates are also contemplated in the present invention as being detected by the methods of the present invention through the detection of Epo-responsive genes. Non-limiting examples of such Epo conjugates are found in U.S. Pat. No. 7,128,913 issued to Burg, et al., on Oct. 31, 2006, which is incorporated herein by reference. Furthermore, Epo derivatives comprising substituted amino acids are also contemplated by the present invention as being detectable for their ability to modulate Epo-responsive genes in vivo providing that they have in vivo activity.

The methods of the present invention are not limited to detecting Epo-responsive genes modulated by Epo, Epo derivatives or Epo mimetics. The methods of the present invention are also capable of detecting the modulation of Epo-responsive genes after stimulation of the Epo-receptor by anti-Epo receptor antibodies. Such antibodies are known in the art as shown, for example, by U.S. Pat. No. 6,998,124, issued to Erickson-Miller, et al., on Feb. 14, 2006, which is incorporated herein by reference.

The methods of the present invention also include the detection of recombinant Epo including Epo as expressed in insect cell systems, via, for example, baculovirus and/or related vectors (see, for example, U.S. Pat. No. 6,103,526, issued Aug. 15, 2000 to Smith et al., and U.S. Pat. No. 5,888,774 issued Mar. 30, 1999 to Delcuve, both of which is incorporated herein by reference). The production of Epo in recombinant systems, including insect systems, are well known in the art.

The Epo-responsive gene detected by the methods of the present invention may be any Epo-responsive gene including, but not limited to podocalyxin, oscosatin and growth differentiation factor-3. In a preferred embodiment, the Epo-responsive gene detected by the methods of the present invention is podocalyxin.

The Epo-responsive gene may be detected by, for example, any method known in the art as and described above and below in the Exemplification section.

The present invention is not limited to any particular circulating erythroid cells providing the cells are responsive to Epo, Epo derivatives or Epo mimetics, for example, by modulating the expression of Epo-responsive genes. Said erythroid cells may be selected from, for example, one or more of reticulocytes, erythroblasts and red blood cells.

Although the present invention is not limited by theory, the following is provided to help in better understanding the present invention.

Although the present invention is not limited by theory, Epo's capacity to promote red cell production was ascribed largely to anti-apoptotic effects on erythroid progenitor pools. Via the gene profiling of primary bone marrow erythroblasts of the present invention, however, Epo is now revealed to down-modulate chemokine receptor-4 (Cxcr4) and integrin alpha-4 (Itga4); to selectively up-modulate the expression of growth differentiation factor-3 (Gdf3), oncostatin-M (Onco-M) and the sialomucin, podocalyxin like-1 (PODXL); and to act in a novel migration and/or adhesion regulatory mode. For PODXL, its marked Epo dose-dependent induction was discovered ex vivo in $Kit^{pos}CD71^{high}$ pro-erythroblasts, and was sustained at subsequent $Kit^{neg}CD71^{high}$ and $Ter119^{pos}$ stages. As administered in vivo, Epo rapidly induced PODXL expression in not only $Kit^{pos}CD71^{high}$ and $CD71^{high}Ter119^{pos}$ progenitors, but also marrow-resident reticulocytes. This further was accompanied by an early Epo-dependent release of reticulocytes to blood. As studied in erythroblasts expressing knocked-in minimal Epo receptor (EpoR) alleles, efficient PODXL induction proved to depend upon an EpoR-PY343 Stat5 binding site. In mice expressing a phosphotyrosine-null EpoR-HM allele, compromised PODXL expression further correlated with an abnormal representation of anucleated red cells in marrow (and with compromised Epo-induced production of circulating $PODXL^{pos}$ reticulocytes). Based on the results of the present invention, Epo, dynamically modulated the above select cytokines and cell surface adhesion molecules (including PODXL) and thereby modifies a unique erythroid progenitor cell niche, mobilizes early stage erythroblasts from stromal compartments and stimulates late reticulocyte emigration to blood.

Recently, it was discovered that a core EpoR/Jak2 signaling axis which supports steady-state erythropoiesis, interestingly fails to support accelerated red cell production during anemia (Menon, M. P., et al., 2006. Signals for stress erythropoiesis are integrated via an erythropoietin receptor-phosphotyrosine-343-Stat5 axis. *J Clin Invest* 116:683-694). Efficient stress erythropoiesis is rescued, however, upon the selective restoration of EpoR/PY343/Stat5 signaling (Menon, M. P., et al., 2006. *J Clin Invest* 116:683-694). These findings prompted a search for new Epo- (and Stat5-)

response genes that might promote stress erythropoiesis. As detailed in the Exemplification section, below, this involved the first-time profiling of such genes in primary bone marrow-derived erythroblasts. Outcomes revealed Epo regulation of several proposed niche modifying factors including growth differentiation factor-3 (Gdf3) (Levine, A. J., and Brivanlou, A. H. 2006. GDF3 at the crossroads of TGF-beta signaling. *Cell Cycle* 5:1069-1073), oncostatin-M (Onco-M) (Tanaka, M., and Miyajima, A. 2003. Oncostatin M, a multifunctional cytokine. *Rev Physiol Biochem Pharmacol* 149:39-52), chemokine receptor-4 (Cxcr4) (Kucia, M., et al., 2005. Trafficking of normal stem cells and metastasis of cancer stem cells involve similar mechanisms: pivotal role of the SDF-1-CXCR4 axis. *Stem Cells* 23:879-894), integrin alpha-4 (Itga4) (Scott, L. M., et al., 2003. Deletion of alpha4 integrins from adult hematopoietic cells reveals roles in homeostasis, regeneration, and homing. *Mol Cell Biol* 23:9349-9360; Arroyo, A. G., et al., 1999. Alpha4 integrins regulate the proliferation/differentiation balance of multilineage hematopoietic progenitors in vivo. *Immunity* 11:555-566) and the CD34-related sialomucin, podocalyxin like-1 (PODXL) (Barton Furness, S. G., and McNagny, K. 2006. Beyond mere markers: functions for CD34 family of sialomucins in hematopoiesis. *Immunol Res* 34:13-32).

Among this novel set of Epo-modulated factors, Onco-M and Gdf3 are secreted cytokines Onco-M acts via its JAK- and Stat-coupled hetero-dimeric receptor (Tanaka, M., et al., 2003. Targeted disruption of oncostatin M receptor results in altered hematopoiesis. *Blood* 102:3154-3162) and can affect cell growth, differentiation and/or migration in tissue and context specific fashions (Tanaka, M., and Miyajima, A. 2003. Oncostatin M, a multifunctional cytokine *Rev Physiol Biochem Pharmacol* 149:39-52; Jorcyk, C. L., et al., 2006. Oncostatin M induces cell detachment and enhances the metastatic capacity of T-47D human breast carcinoma cells. *Cytokine* 33:323-336). Gdf3 acts as a TGF-beta receptor family antagonist, and is best characterized by its effects on embryonic dorsal axis formation (Levine, A. J., and Brivanlou, A. H. 2006. GDF3 at the crossroads of TGF-beta signaling. *Cell Cycle* 5:1069-1073; McPherron, A. C., and Lee, S. J. 1993. GDF-3 and GDF-9: two new members of the transforming growth factor-beta superfamily containing a novel pattern of cysteines. *J Biol Chem* 268:3444-3449). Cxcr4 and Itga4, respectively, are the seven trans-membrane receptor for the Cxc chemokine SDF-1 (Elisseeva, E. L., et al., 2000. NMR studies of active N-terminal peptides of stromal cell-derived factor-1. Structural basis for receptor binding. *J Biol Chem* 275:26799-26805), and an integrin alpha-4 subunit that (as associated with beta-1 integrin) mediates binding to vascular cell adhesion molecule 1 (VCAM-1), fibronectin, and paxillin (Scott, L. M., et al., 2003. Deletion of alpha4 integrins from adult hematopoietic cells reveals roles in homeostasis, regeneration, and homing. *Mol Cell Biol* 23:9349-9360; Peterson, J. A., et al., 2005. Heparin II domain of fibronectin uses alpha4beta1 integrin to control focal adhesion and stress fiber formation, independent of syndecan-4. *J Biol Chem* 280:6915-6922; Rose, D. M. 2006. The role of the alpha4 integrin-paxillin interaction in regulating leukocyte trafficking *Exp Mol Med* 38:191-195).

PODXL is a sulphated sialomucin that is expressed at high levels by renal podocytes, and supports glomerular diaphragm slit formation via anti-adhesive and/or charge repulsion effects (Barton Furness, S. G., and McNagny, K. 2006. Beyond mere markers: functions for CD34 family of sialomucins in hematopoiesis. *Immunol Res* 34:13-32; Dekan, G., Gabel, C., and Farquhar, M. G. 1991. Sulfate contributes to the negative charge of podocalyxin, the major sialoglycoprotein of the glomerular filtration slits. *Proc Natl Acad Sci USA* 88:5398-5402). However, PODXL also is a marker for developing hemangioblasts and hematopoietic stem cells (Doyonnas, R., et al., 2005. Podocalyxin is a CD34-related marker of murine hematopoietic stem cells and embryonic erythroid cells. *Blood* 105:4170-4178), and can apparently exert anti-adhesive effects in cell migratory contexts (Barton Furness, S. G., and McNagny, K. 2006. *Immunol Res* 34:13-32). Within the erythroid lineage, the presently discovered marked Epo-induction of PODXL in (pro)erythroblasts is hypothesized to promote emigration from an early stage stromal niche, as well as reticulocyte egress from marrow, specifically during anemia.

In bone marrow, niches for stem cells have been characterized at sinusoidal endothelia which affect self-renewal vs. differentiation (Wilson, A., and Trumpp, A. 2006. Bone-marrow haematopoietic-stem-cell niches. *Nat Rev Immunol* 6:93-106). Similarly, B-cell progenitor fates have been shown to depend on niche-associated interactions with sinusoidal reticular, and $CXCL12^{high}$ stromal cells (Nagasawa, T. 2006. Microenvironmental niches in the bone marrow required for B-cell development. *Nat Rev Immunol* 6:107-116). Erythroid islands also clearly exist, are broadly distributed in marrow and are comprised of approximately ten erythroid cells plus a central resident macrophage (Chasis, J. A. 2006. Erythroblastic islands: specialized microenvironmental niches for erythropoiesis. *Curr Opin Hematol* 13:137-141). Island formation depends in part upon ICAM4 and alpha-5 integrin interactions, and appears to affect primarily late-stage erythroblast maturation (Chasis, J. A. 2006. *Curr Opin Hematol* 13:137-141; Lee, G., et al., 2006. Targeted gene deletion demonstrates that cell adhesion molecule ICAM-4 is critical for erythroblastic island formation. Blood, September 15; 108 (6):2064-2071). By comparison, the presently characterized unique erythroid niche includes early stage erythroblasts, predicted stromal components, and several associated (but previously undescribed) Epo target genes. Overall, findings indicate that Epo functions as more than a simple survival factor and dynamically modifies the erythroblast cell surface and its microenvironment.

EXEMPLIFICATION

Abbreviations used herein: Bcl-2, B-cell leukemia/lymphoma 2; Bcl-xl, Bcl-2 like-1; CFUe, colony-forming unit-erythroid; Cis, cytokine-inducible Src-homology 2-containing protein; Cxcr4, chemokine receptor 4; Epo, erythropoietin; EpoR, erythropoietin receptor; EpoR-H, knocked-in EpoR allele truncated at amino acid 361; EpoR-HM, Y343F-mutation within EpoR-H; EVA, exploratory visual analysis; FBS, fetal bovine serum; Gdf3, growth differentiation factor 3; ICAM4, intercellular adhesion molecule 4; IRF, immature reticulocyte fraction; Itga4, integrin alpha-4; JAK2, janus kinase 2; Onco-M, oncostatin-M; OSMR, oncostatin-M receptor; mTOR, mammalian target of rapamycin; PODXL, podocalyxin-like; SP34-EX, SP34-based serum-free erythroid expansion medium; SCF, stem cell factor; SDF-1, stromal derived factor-1; STAT, signal transducer and activator of transcription; TRAIL, TNF-related apoptosis inducing ligand; wt, wild-type; VCAM-1, vascular cell adhesion molecule 1; VLA4, very late antigen 4. All citations are incorporated herein by reference.

Materials and Methods

Mice: Mice expressing EpoR-HM and EpoR-H alleles (and congenic controls) were as described (Menon, M. P., et al., 2006. Signals for stress erythropoiesis are integrated via an erythropoietin receptor-phosphotyrosine-343-Stat5 axis. *J*

Clin Invest 116:683-694; Zang, H., et al., 2001. The distal region and receptor tyrosines of the Epo receptor are nonessential for in vivo erythropoiesis. *Embo J* 20:3156-3166), and were used in IACUC-approved procedures at 8-12 weeks. Hematocrits and reticulocytes were assayed by microcentrifugation, and flow cytometry (ReticCount-Reagent™, BD Biosciences) (Menon, M. P., et al., 2006. Signals for stress erythropoiesis are integrated via an erythropoietin receptor-phosphotyrosine-343-Stat5 axis. *J Clin Invest* 116:683-694). Epoietin-alpha was administered intraperitoneally at 1 and 24 hours at the doses indicated.

Primary erythroblast preparations: Marrow was flushed from femurs and tibiae in Iscove's modified Dulbecco's medium (IMDM, Invitrogen #12440-053) containing 2% FBS, passed through a 40 µm strainer, washed and resuspended in 1 mL of phosphate buffered saline (PBS) (Invitrogen #14190-144). Following a two-minute exposure to 9 mL of buffered 0.8% ammonium chloride (Stem Cell Technologies), 10×PBS (1.1 mL) was added and cells were collected through 50% FBS in PBS and washed in IMDM. Ex vivo culture was at $8 \times 10^5$ cells/mL in StemPro-34 (Invitrogen) supplemented with 2.5 U/mL Epo, 100 ng/mL mSCF, 1 uM dexamethasone, 1 uM beta-estradiol, 40 ng/mL IGF-1, 75 ug/mL h-transferrin, (Sigma #T0665), 0.5% BSA (Stem Cell Technologies, #9300), 0.1 mM 2-mercaptoethanol and 1.5 mM L-glutamine (i.e., "5P34-EX" medium) (Menon, M. P., et al., 2006. Signals for stress erythropoiesis are integrated via an erythropoietin receptor-phosphotyrosine-343-Stat5 axis. *J Clin Invest* 116:683-694). At day-3 of expansion, $CD71^{pos}Ter119^{neg}$ erythroblasts were isolated by two rounds of $Lin^{pos}$ cell depletion (Stem Cell Technologies). $Kit^{pos}CD71^{high}$ erythroblasts were purified further by CD117 MACS selection (Miltenyi Biotech).

Gene profiling, data analysis, and RT-PCR: Purified $Kit^{pos}CD71^{pos}$ cells were cultured for 6 hours in IMDM containing 0.5% BSA, transferrin (10 µg/mL), (Sigma T0665) and insulin (15 ng/mL) (Invitrogen #41400-045). Cells then were exposed to Epo (+/−5 U/mL) for 90 minutes, and RNA was isolated using Trizol reagent (Invitrogen) and robotic extraction (Autogen Prep245) (#). Biotin-cRNA syntheses used 3 µg of RNA, and hybridizations were to Affymetrix 430-2.0 arrays. Signals were processed via GeneChip® 3000 scanning, and GCOS software. In data mining, GeneTraffic, exploratory visual analysis (EVA), ChipInspector and BiblioSphere Pathway-Edition software were used. RT utilized TURBO DNase (Ambion) and Superscript III (Invitrogen). PCR primer pairs (SuperArray Bioscience) were: Onco-M, NM001013365; Gdf3, NM008108; Podxl, NM013723; Itga4, NM010576; Cxcr4, NM009911; β-actin, NM_007393. Quantitative PCR utilized iQ™ SYBR® Green and an i-Cycler (BIO-RAD).

Flow cytometry: In flow cytometry (BD FACScalibur), $1 \times 10^6$ cells were incubated at 4° C. with 1 µg of rat IgG in 0.2 mL of PBS, 0.5% BSA (15 minutes) and for 45 minutes with 1 µg of primary antibodies as: APC-Ter119 or APC-anti-Kit; PE-anti-CD71 (BD Biosciences, #557909, #553356 #553267); and biotin anti-PODXL (R&D Systems, #BAF1556) (or biotin-goat IgG as a negative control). Bound PODXL antibodies were detected using either AlexaFluor-488 or AlexaFluor-647 streptavidin (Molecular Probes). FITC-anti-Cxcr4 and PE-CD49d were from BD Biosciences, and Southern Biotech. Nucleated erythroblasts were assayed by co-staining with PE-Ter119 (BD Biosciences, #553673) and DRAQ5 (10 µM) (Alexis Biochemicals), and Retic-COUNT. Reticulocytes were co-stained with anti-PODXL, and Retic-COUNT. In all experiments, equivalent numbers of gated events were analyzed.

Microscopy: Cytospin analyses ($1 \times 10^5$ cells) involved slide-centrifugation (15 minutes, 300 rpm, Hettich Universal-16A cyto-centrifuge) and Dip-Stain reagent staining (Volu-Sol #V55016). In confocal microscopy (Leica, LTCS-SP), staged erythroblasts were isolated, immuno-stained, washed, fixed in 4% paraformaldehyde and co-stained with Hoechst 34580 (Molecular Probes).

Results

Figure 1B:
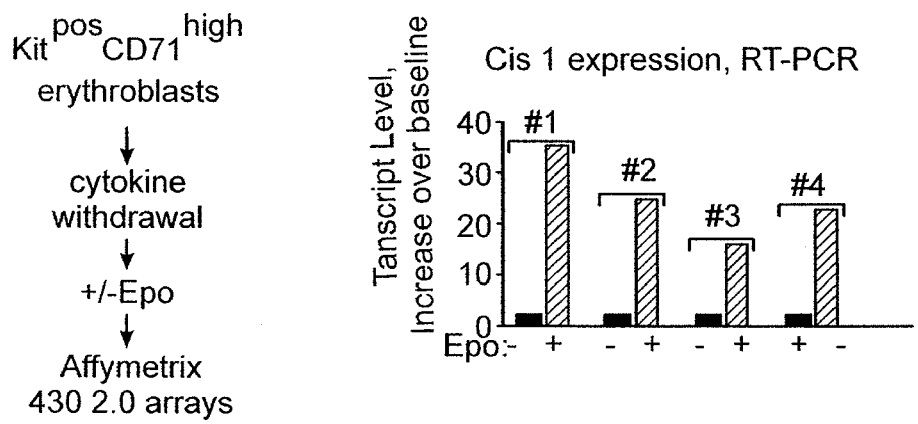
Figure 1C:
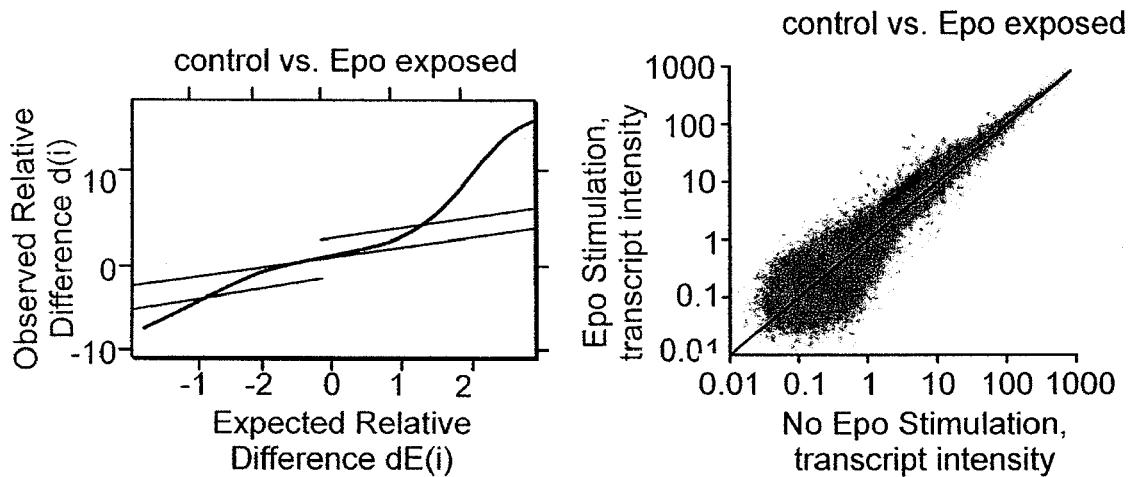

Experiments first investigated possible Epo regulation of novel response genes in murine bone marrow-derived erythroblasts. This primary target population was generated via progenitor cell short-term expansion of erythroid progenitor cells in an optimized serum-free SP34-EX system (Menon, M. P., et al., 2006. Signals for stress erythropoiesis are integrated via an erythropoietin receptor-phosphotyrosine-343-Stat5 axis. *J Clin Invest* 116:683-694). At day 3.5, $Kit^{pos}CD71^{high}Ter119^{neg}$ erythroblasts were isolated (from n=4 mice at ≧99% purity) via $lin^{pos}$ depletion, and $Kit^{pos}$ cell selection (FIG. 1A). These staged (and maximally Epo-responsive erythroblasts) were then cultured for 6 hours in the absence of hematopoietic cytokines, and stimulated with Epo for 90 minutes. From these, and parallel unstimulated cultures, biotin-cRNAs and DNAs were prepared. Quantitative PCR also was used to confirm high-level induction of Cis1 (FIG. 1B), a known Epo-response gene (Matsumoto, A., et al., 1997. CIS, a cytokine inducible SH2 protein, is a target of the JAK-STAT5 pathway and modulates STAT5 activation. *Blood* 89:3148-3154). In FIG. 1C, relative differences for microarray outcomes are illustrated. Overall, approximately 200 Epo response genes were identified with high statistical significance.

For Affymetrix 430-2.0 array profiling outcomes, a focus was narrowed to transcripts that were modulated two-fold or more by Epo, and in addition corresponded to cell surface or secreted factors (i.e., potential niche modifiers). This selectively included two secreted cytokines, Gdf3 (Levine, A. J., and Brivanlou, A. H. 2006. GDF3 at the crossroads of TGF-beta signaling. *Cell Cycle* 5:1069-1073) and Onco-M (Tanaka, M., and Miyajima, A. 2003. Oncostatin M, a multifunctional cytokine. *Rev Physiol Biochem Pharmacol* 149: 39-52), and the adhesion and/or migration factors Cxcr4 (Kucia, M., et al., 2005. Trafficking of normal stem cells and metastasis of cancer stem cells involve similar mechanisms: pivotal role of the SDF-1-CXCR4 axis. *Stem Cells* 23:879-894), Itga4 (Scott, L. M., et al., 2003. Deletion of alpha4 integrins from adult hematopoietic cells reveals roles in homeostasis, regeneration, and homing. *Mol Cell Biol* 23:9349-9360; Arroyo, A. G., et al., 1999. Alpha4 integrins regulate the proliferation/differentiation balance of multilineage hematopoietic progenitors in vivo. *Immunity* 11:555-566) and PODXL (Barton Furness, S. G., and McNagny, K. 2006. Beyond mere markers: functions for CD34 family of sialomucins in hematopoiesis. *Immunol Res* 34:13-32) (FIG. 1D). Profiling data specifically indicated 10.8- and 3.1-fold induction of Onco-M and Gdf3; 1.3- and 2.2-fold down-modulation of Itga4 and Cxcr4; and 15.3-fold induction of PODXL. Follow-up quantitative RT-PCR analyses confirmed 16.3- and 2.2-fold induction of Onco-M and Gdf3, respectively, 2.3- and 2.9-fold down-modulation of Itga4 and Cxcr4, respectively, and 8.9-fold induction of PODXL (FIG. 1E).

Gdf3 is a TGF-beta antagonist that inhibits classical TGF-beta and BMP signaling (Levine, A. J., and Brivanlou, A. H. 2006. GDF3 at the crossroads of TGF-beta signaling. *Cell Cycle* 5:1069-1073), and is expressed predominantly in bone marrow, spleen, thymus and adipocytes (Levine, A. J., and Brivanlou, A. H. 2006. *Cell Cycle* 5:1069-1073). Its expression by erythroid progenitor cells has not previously been described. Onco-M is a pleiotropic cytokine (Tanaka, M., and Miyajima, A. 2003. Oncostatin M, a multifunctional cytokine *Rev Physiol Biochem Pharmacol* 149:39-52), but disruption of its receptor selectively decreases erythro-megakaryocytic potentials (Tanaka, M., et al., 2003. Targeted disruption of oncostatin M receptor results in altered hematopoiesis. *Blood* 102:3154-3162). Onco-M and Gdf3 therefore are implicated as uniquely activated cytokine components of an Epo signaling axis. Cxcr4 and Itga4 were each rapidly down-modulated several-fold by Epo (FIGS. 1D and 1E). Cxcr4 is a seven-transmembrane receptor for stromal derived factor-1 (SDF-1) and can support niche homing by several stem and progenitor cell types (Kucia, M., et al., 2005. Trafficking of normal stem cells and metastasis of cancer stem cells involve similar mechanisms: pivotal role of the SDF-1-CXCR4 axis. *Stem Cells* 23:879-894; Son, B. R., et al., 2006. Migration of bone marrow and cord blood mesenchymal stem cells in vitro is regulated by stromal-derived factor-1-CXCR4 and hepatocyte growth factor-c-met axes and involves matrix metalloproteinases. *Stem Cells* 24:1254-1264). Within bone marrow, SDF-1 further can remain associated with stromal cell surfaces, and recruit $Cxcr4^{pos}$ cells (Kucia, M., et al., 2005. *Stem Cells* 23:879-894). Itga4 preferentially binds VCAM1 and fibronectin (and is also important for early hematopoietic progenitor cell migration and development) (Arroyo, A. G., et al., 1999. Alpha4 integrins regulate the proliferation/differentiation balance of multilineage hematopoietic progenitors in vivo. *Immunity* 11:555-566). For both Cxcr4 and Itga4, Epo-dependent down-modulation in $Kit^{pos}CD71^{high}$ cells therefore is predicted to promote erythroblast transit from stromal cell compartments.

The CD34-related sialomucin, PODXL, in contrast, was strongly up-modulated by Epo in $Kit^{pos}CD71^{high}$ erythroblasts (FIG. 1D, E). PODXL is best known to be expressed by renal podocytes, and to support filtration slit formation (Barton Furness, S. G., and McNagny, K. 2006. Beyond mere markers: functions for CD34 family of sialomucins in hematopoiesis. *Immunol Res* 34:13-32). However, PODXL also marks developing vascular endothelial cells, and hematopoietic stem cells (Barton Furness, S. G., and McNagny, K. 2006. *Immunol Res* 34:13-32; Doyonnas, R., et al., 2005. Podocalyxin is a CD34-related marker of murine hematopoietic stem cells and embryonic erythroid cells. *Blood* 105:4170-4178). For PODXL, Cxcr4 and Itga4, modulation at the erythroblast cell surface was further examined by flow cytometric assays. In keeping with transcript analyses, Epo up-modulated PODXL, and down-modulated Cxcr4 in $Kit^{pos}CD71^{high}$ erythroblasts with dose-dependency (FIG. 1F). Cell surface levels of Itga4, however, were not significantly affected by Epo over a 24-hour time frame. For Itga4, this might reflect a long half-life (or possibly the opposing actions of factors which promote Itga4 expression).

Figure 2A:
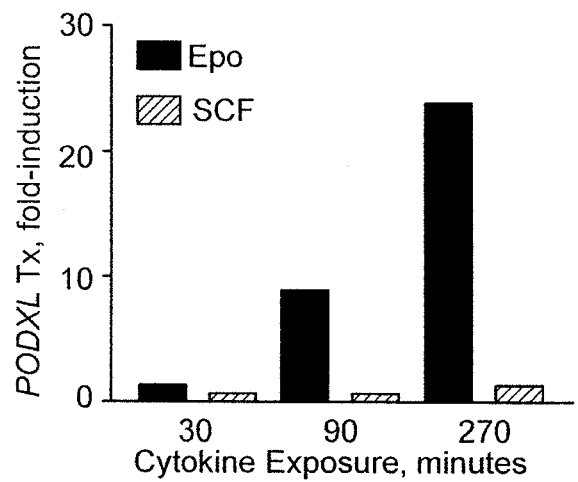
FIG. 2. Epo-specific PODXL induction in developmentally staged marrow erythroblasts. A) In MACS purified $Kit^{pos}CD71^{high}$ erythroblasts, time-courses of EPO, and SCF induction of PODXL expression (following cytokine withdrawal) were assessed by quantitative RT-PCR. B) In SP34-EX expansion cultures, cell surface PODXL expression among $Kit^{pos}CD71^{high}$, $Kit^{neg}CD71^{high}$, and $Kit^{neg}CD71^{high}Ter119^{pos}$ erythroblasts was analyzed by flow cytometry. Frequencies of PODXL$^{pos}$ cells are indicated for bisected PODXL$^{low}$ and PODXL$^{high}$ subpopulations. C) For the above stages of developing erythroblasts, cytospin morphologies for FACS-purified populations also are shown.
Figure 2B:
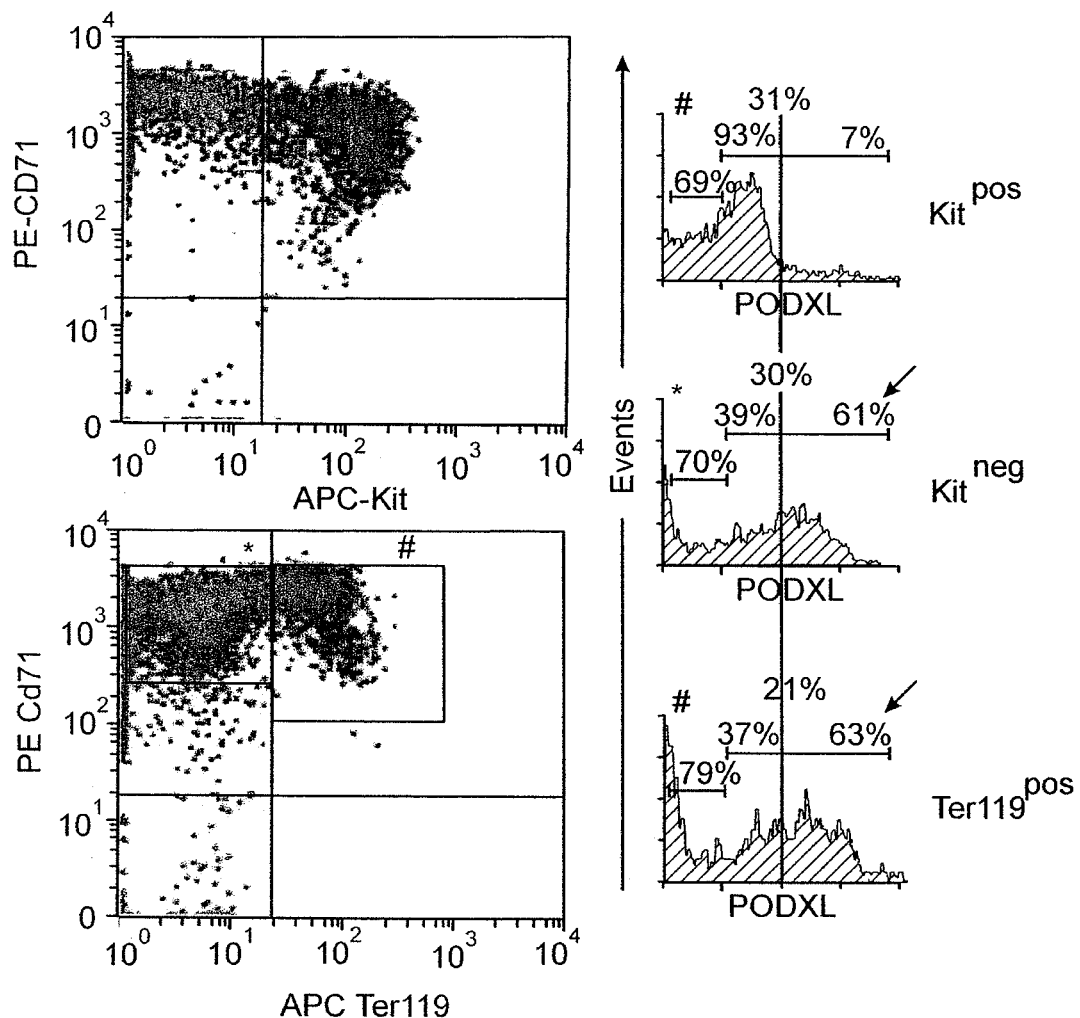
Figure 2C:
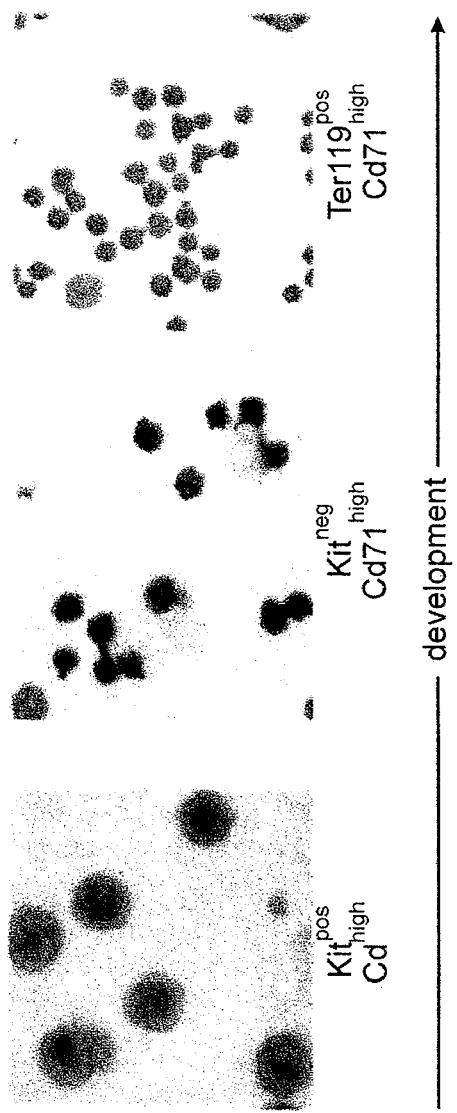

The extent to which PODXL's strong up-modulation might be affected specifically by Epo was next assessed. $Kit^{pos}CD71^{high}$ cells were isolated, cultured in the absence of hematopoietic growth factors, and stimulated with either Epo or SCF. Time-course analyses revealed an approximate 25-fold induction of PODXL by Epo (FIG. 2A). No such increase was affected by SCF. Epo's ability to modulate PODXL expression within a staged series of erythroblasts also was examined. This included $Kit^{pos}CD71^{high}$, $Kit^{neg}CD71^{high}$ and $Kit^{neg}CD71^{high}Ter119^{pos}$ cells (see FIGS. 2B and 2C for flow cytometry and cytospin characterizations). In $Kit^{neg}CD71^{high}$ cells, PODXL expression increased markedly, and was sustained in late-stage $Ter119^{pos}CD71^{high}$ erythroblasts (FIG. 2B). In addition, among $Kit^{neg}CD71^{high}$ and $CD71^{high}Ter119^{pos}$ erythroblasts, cell surface levels of Epo-induced PODXL expression interestingly appeared to continue to significantly increase (based on relative intensities of PODXL staining) (FIG. 2B).

Figure 3A:
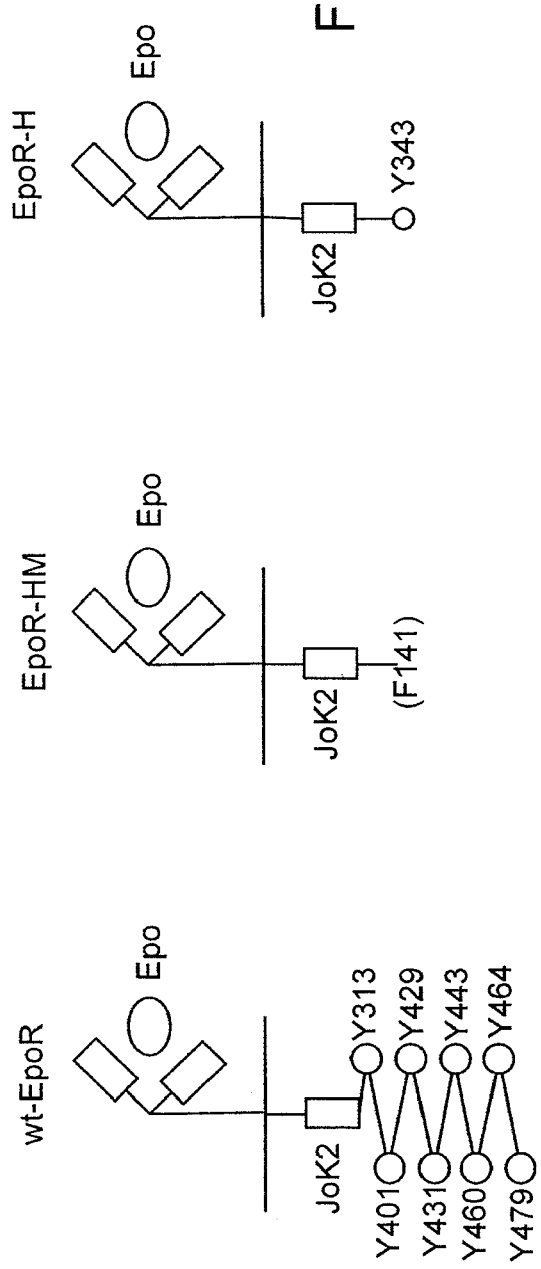
FIG. 3. Epo-induced PODXL expression depends on EpoR/PY343/Stat5 signaling. A) wt-EpoR and minimal knocked-in EpoR-HM and EpoR-H alleles are diagrammed. B) EpoR-HM fails to support efficient Epo-induced PODXL expression—Kit$^{pos}$CD71$^{high}$ erythroblasts from wild-type, EpoR-HM, and EpoR-H marrow, were expanded. At day 2.5, expansion cultures were shifted to SP34-EX medium lacking SCF, and containing Epo at 0.1, 0.4, and 1.6 U/mL. At day 3.5, lin$^{pos}$-depleted cultures were analyzed for PODXL expression by flow cytometry, (B-1, B-2) and confocal microscopy (B-3). Also graphed for wt-EpoR, EpoR-HM and EpoR-H erythroblasts is the fold-induction of PODXL due to Epo (1.6 U/mL) (B-4). C) In silico analyses of predicted STAT elements and STAT/ETS modules in murine PODXL and Cis1 promoters. The occurrences of consensus elements were predicted using Genomatix Chipinspector software.
Figures 1, 3B:
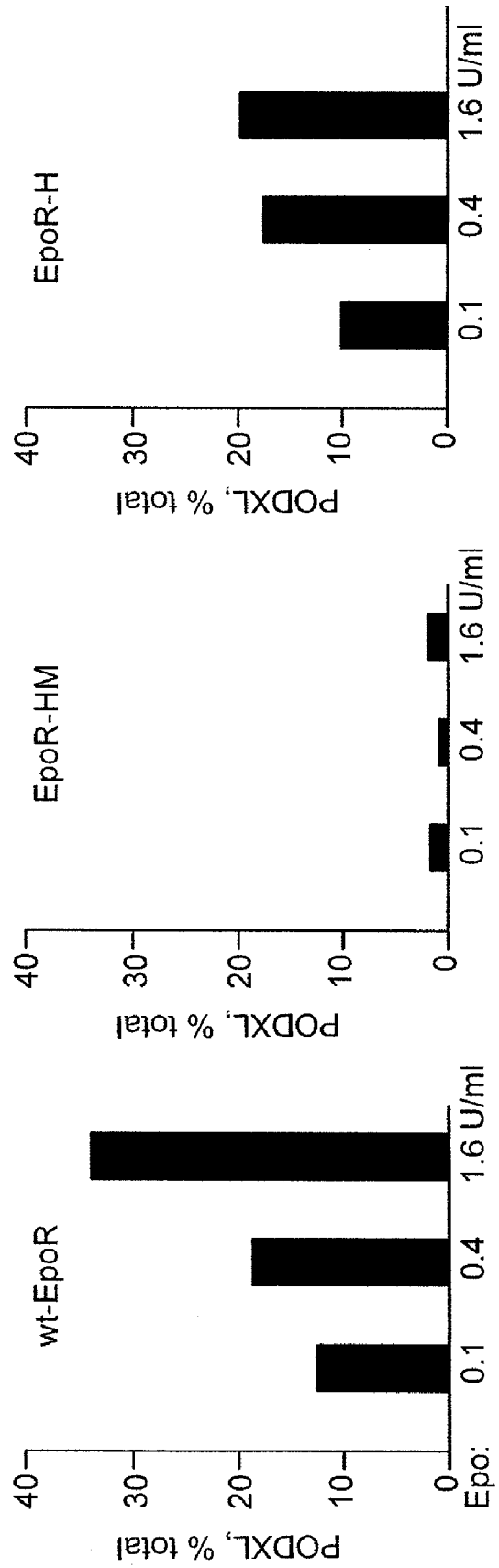

To more mechanistically consider Epo-regulated PODXL expression, induction via knocked-in EpoR-HM and EpoR-H alleles was studied. EpoR-HM retains a membrane proximal box-1 motif, activates JAK2, couples to MEK½ and ERK½ (Menon, M. P., et al., 2006. Core erythropoietin receptor signals for late erythroblast development. *Blood* 107:2662-2672), but otherwise lacks cytoplasmic PY signal transduction factor docking sites. EpoR-H is related, but possesses a selectively restored PY343 Stat5 binding site (FIG. 3A) (Menon, M. P., et al., 2006. Signals for stress erythropoiesis are integrated via an erythropoietin receptor-phosphotyrosine-343-Stat5 axis. *J Clin Invest* 116:683-694). Erythroid cells were expanded from wt-EpoR, EpoR-HM and EpoR-H marrow preparations. $Kit^{pos}CD71^{high}$ erythroblasts then were isolated and analyzed for PODXL expression at the transcript and cell surface levels (FIG. 3B). Each analysis revealed deficient expression in EpoR-HM erythroblasts (PY-null allele), together with a substantial rescue of PODXL expression upon PY343 site restoration in EpoR-H erythroblasts.

Figures 2, 3B:
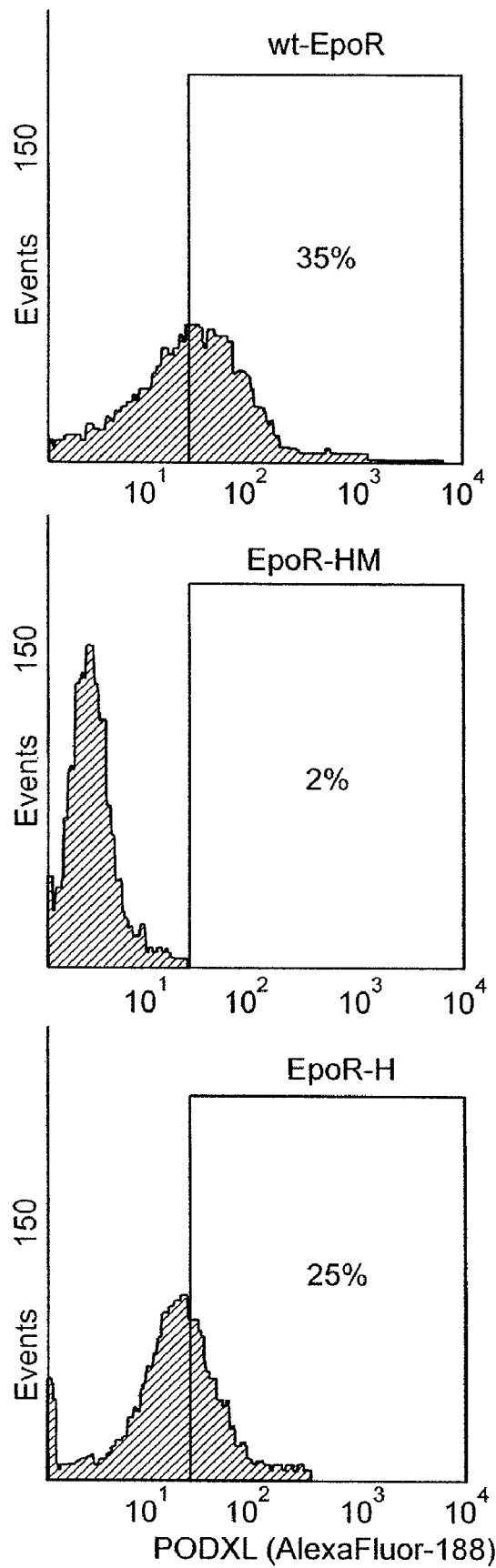
Figures 3, 3B:
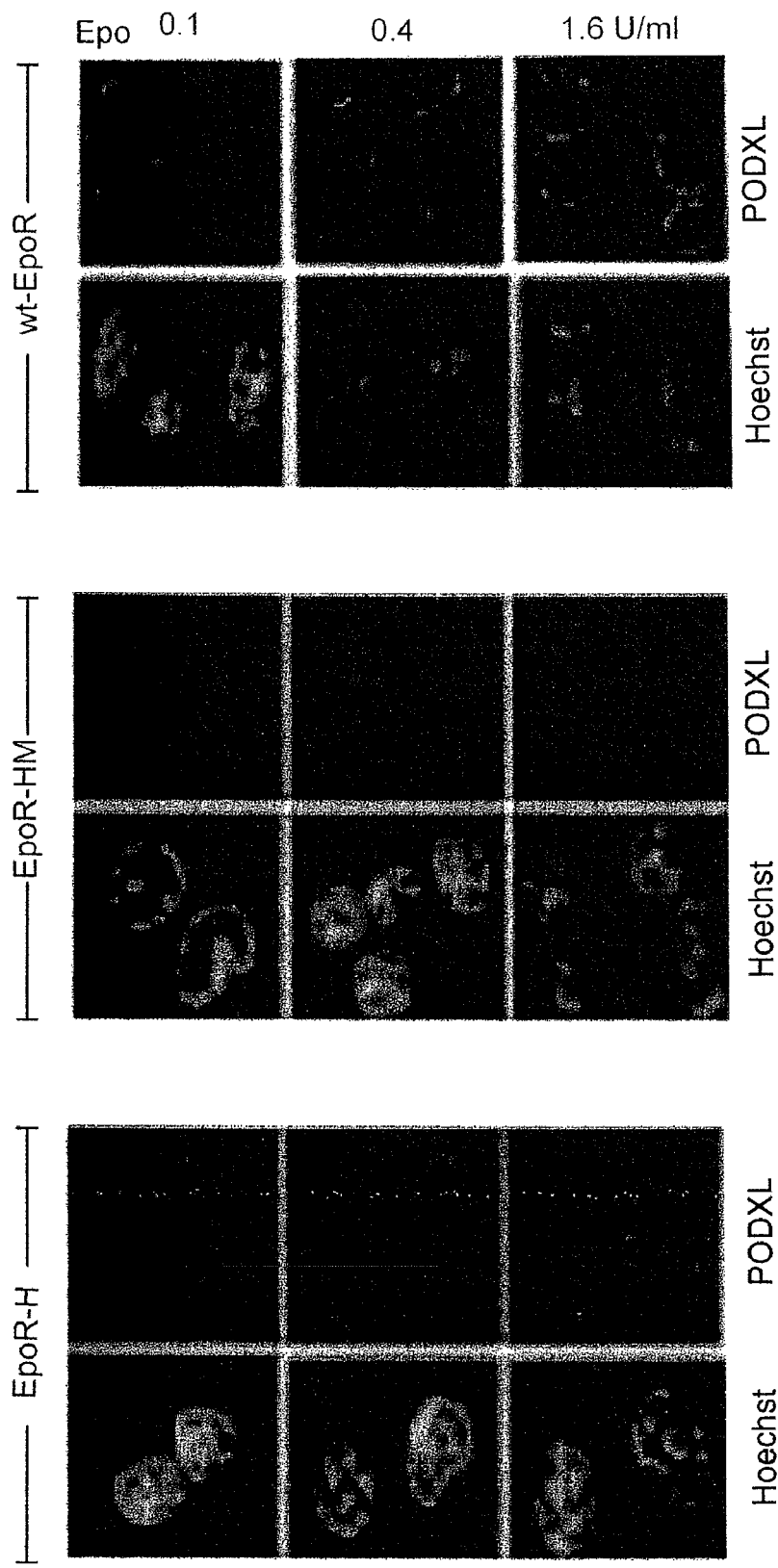
Figures 3, 3B, 4:
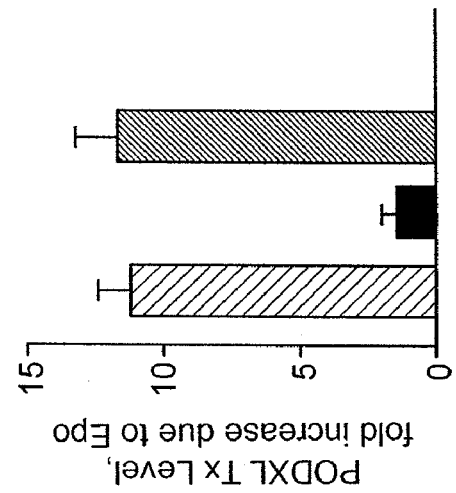
FIG. 4. In vivo Epo dose-dependent expression of PODXL by immature reticulocytes. A) Epo dose-dependent increases in reticulocytes, PODXL$^{pos}$ immature reticulocytes, and PODXL expression levels in wild-type mice—At day-3 post Epo injection (0, 600, 1800 U/mL), increases in peripheral blood reticulocytes, and in PODXL$^{pos}$ immature reticulocytes (IRF, immature reticulocyte fraction) were assayed by flow cytometry (left and center panels). Average PODXL expression levels within the IRF also were assayed based on fluorescence intensity. B) PODXL staining intensities specifically within the IRF compartment, and among stage R4 and R5 reticulocytes are illustrated. Here, wild-type mice were injected with Epo (1200 U/Kg). For peripheral blood sampled at day-3, frequencies of PODXL$^{pos}$ cells within reticulocyte compartments then were determined. C) Epo dose-dependent increases in PODXL$^{pos}$ expression levels (cell surface densities) by R5-stage reticulocytes also are illustrated.
Figure 3C:
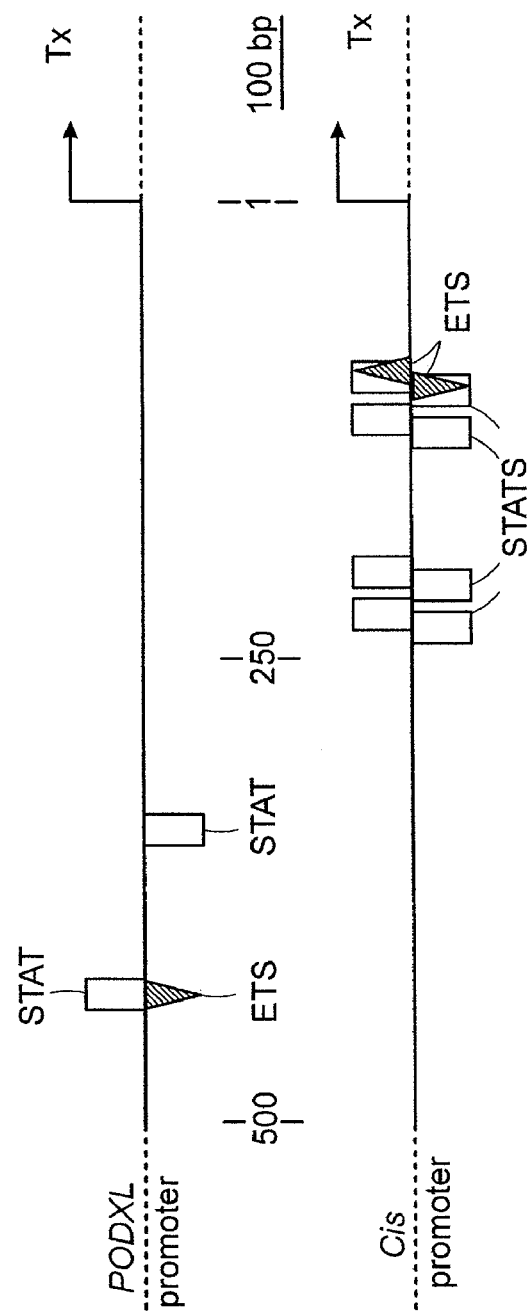

Epo dosing effects on PODXL expression also were examined. Primary erythroblasts from wt-EpoR, EpoR-HM, and EpoR-H were isolated and expanded. At day 2.5, cells were transferred to SP34-EX medium with Epo at 0.1, 0.4, or 1.6 U/mL (and no SCF). After 24 hours, $lin^{pos}$-depleted cell populations were analyzed. In wt-EpoR cells, PODXL expression in low-level Epo (0.1 U/mL) was visible via confocal microscopy, and in flow cytometry was detected on ~12% of erythroblasts (FIG. 3B-1 and 3B-3). Higher dose Epo (1.6 U/mL) boosted frequencies of positive erythroblasts (to ~35%) (FIG. 3B-2), as well as PODXL cell surface densities. In EpoR-HM cells, in contrast, little PODXL was detectable. For EpoR-H cells, confocal images and flow cytometry revealed a substantial (yet partial) restoration of PODXL expression. These experiments indicate that EpoR PY343 (and Stat5) signals are important for Epo regulation of PODXL, but that expression is enhanced by EpoR C-terminal signals. Finally, in silico analyses indicated the occurrence of two consensus STAT elements within the PODXL proximal promoter (FIG. 3C). One further occurred within a STAT/ETS module which was also represented within the Cis1 gene promoter.

Figure 4A:
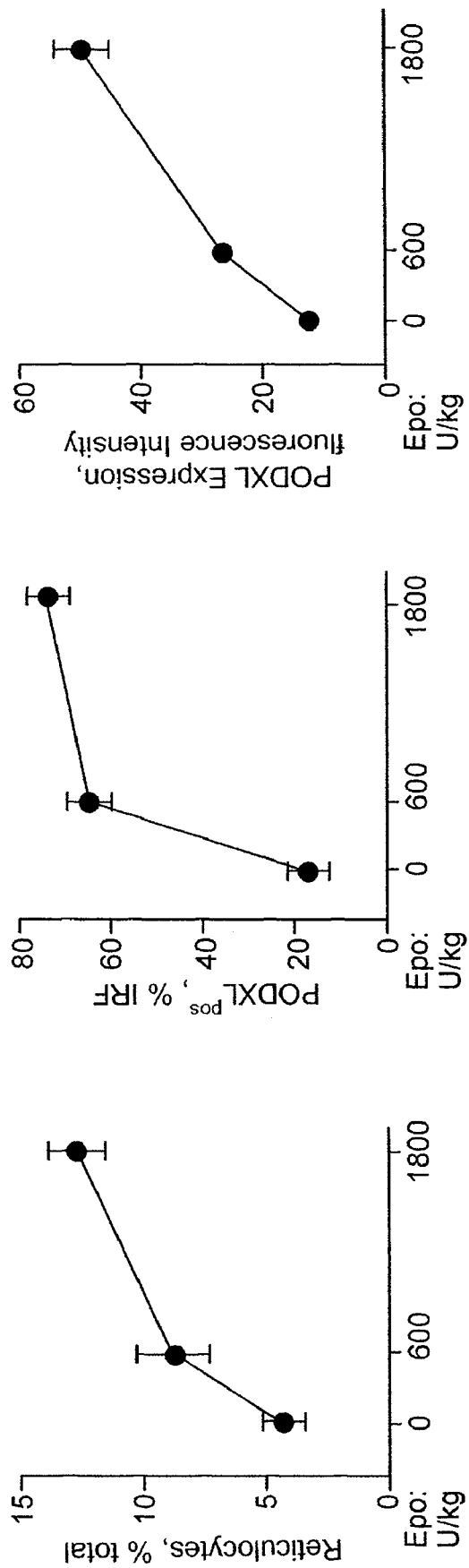
Figure 4B:
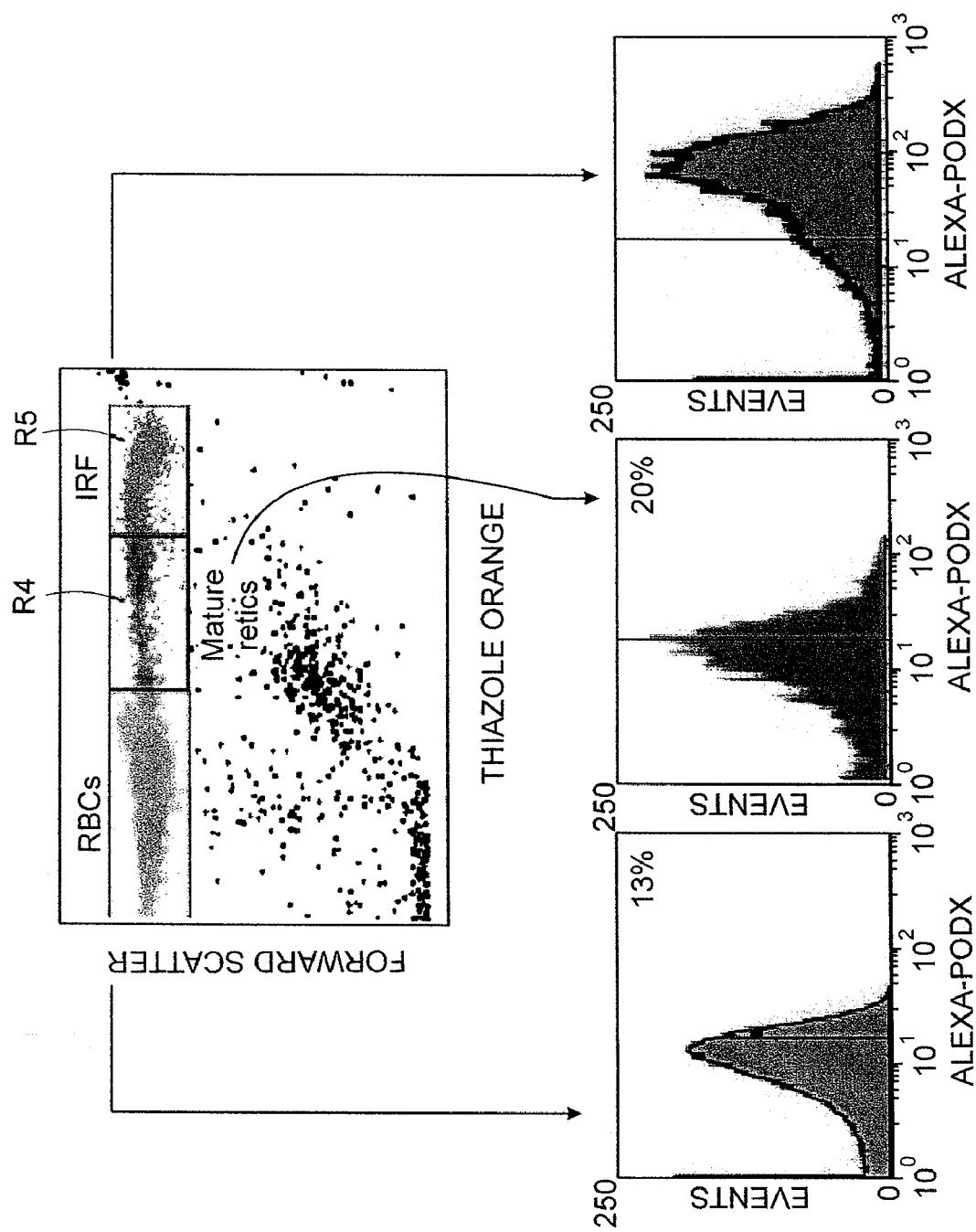
Figure 4C:
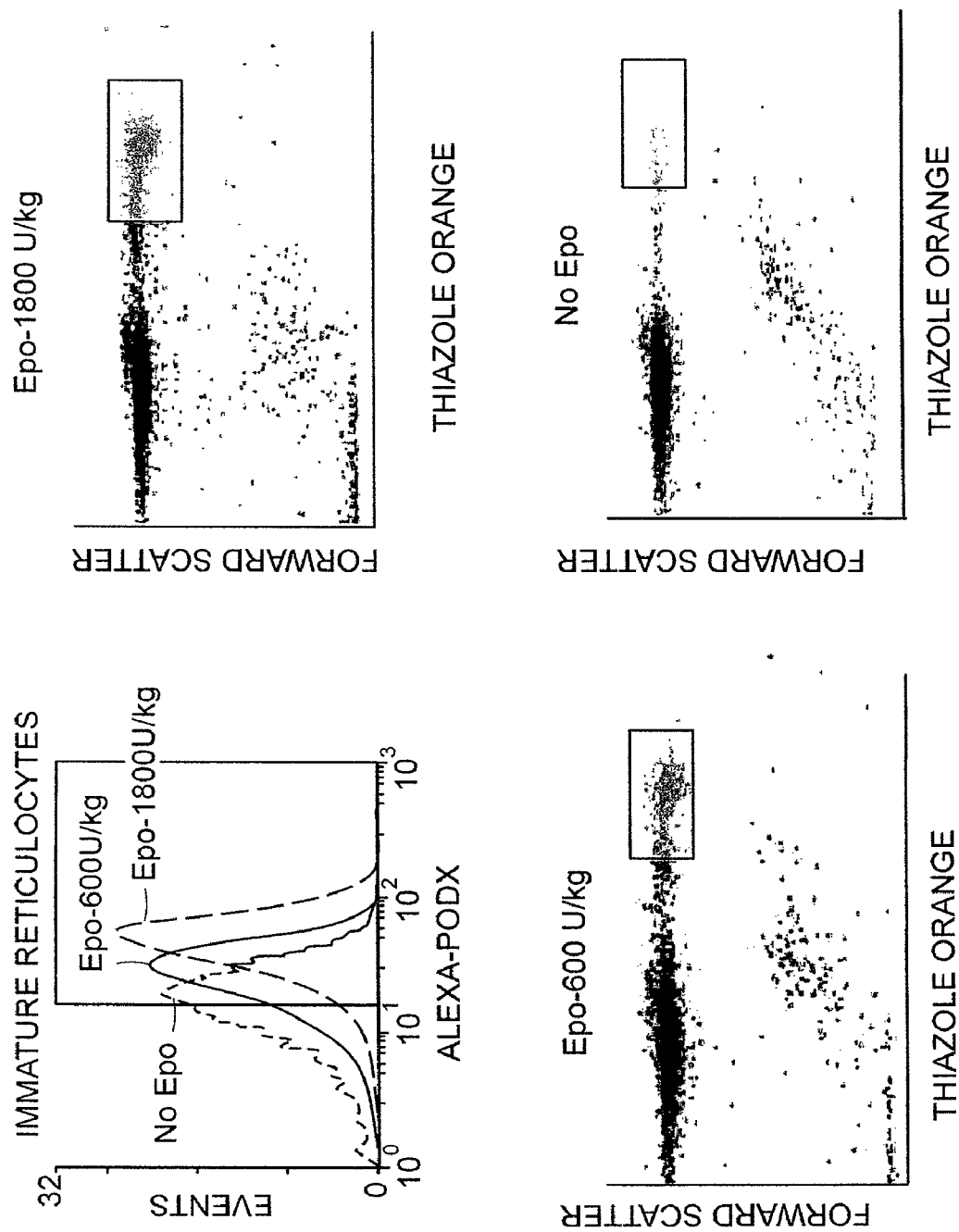

Based on Epo-induced PODXL expression by late-stage erythroblasts ex vivo, whether PODXL expression might persist among reticulocytes in vivo next was tested. Specifically, an Epo dose-response relationship for reticulocyte production first was defined, and peripheral red cells from Epo-injected mice were analyzed for PODXL expression (FIG. 4A). In Epo-injected mice, a low percentage of RBCs (~13%) stained as $PODXL^{pos}$; 20% of mature reticulocytes (R4 stage) were $PODXL^{pos}$ and stained up to five-fold brighter; and 74% of immature reticulocytes (R5 stage) were $PODXL^{pos}$ and stained at high-intensity (IRF, immature reticulocyte fraction) (FIG. 4B). Within the IRF, PODXL densities interestingly also increased in a sharply Epo dose-dependent fashion (FIG. 4C).

Figures 1, 5A:
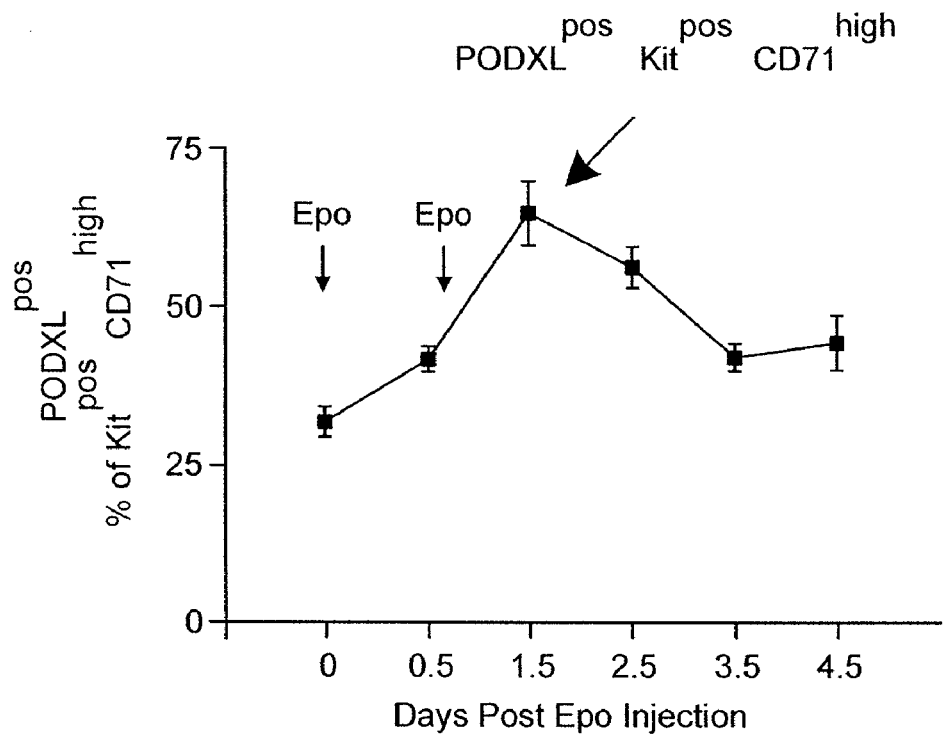
Figures 2, 5A:
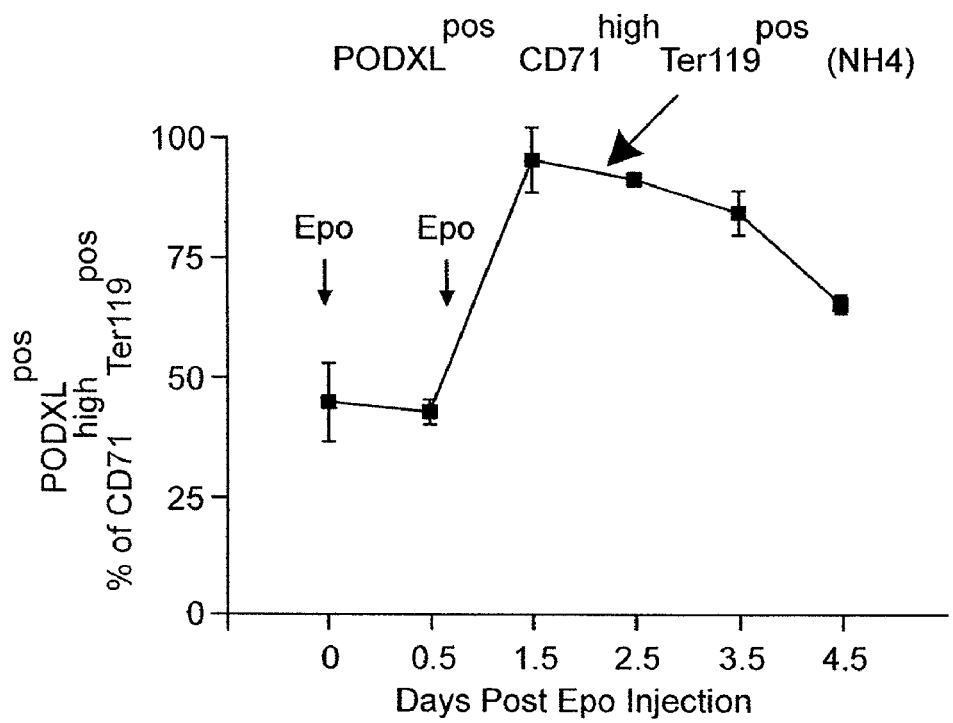
Figures 3, 5A:
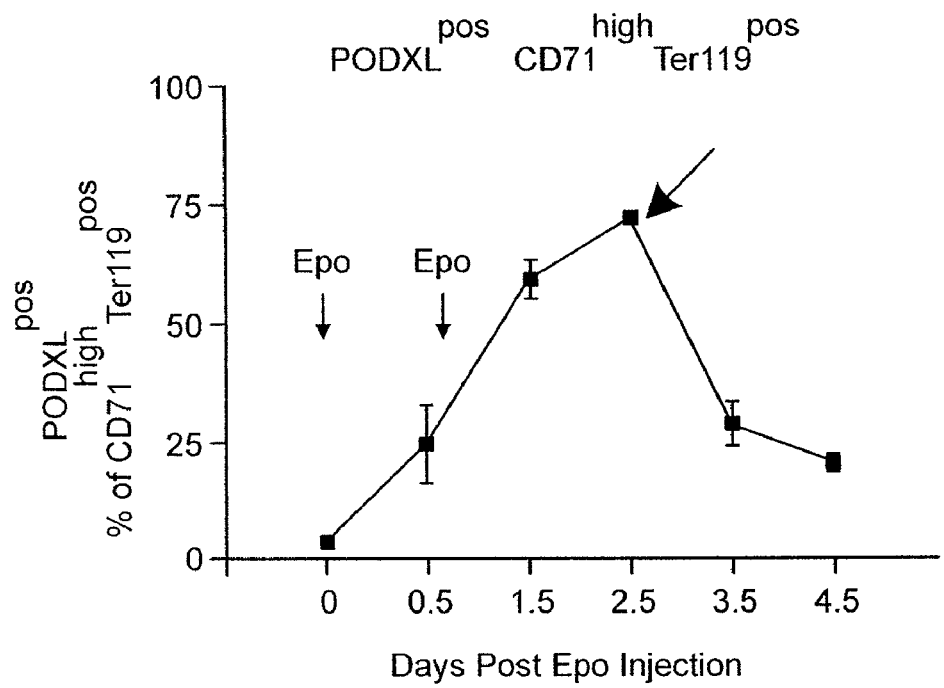
Figures 4, 5A:
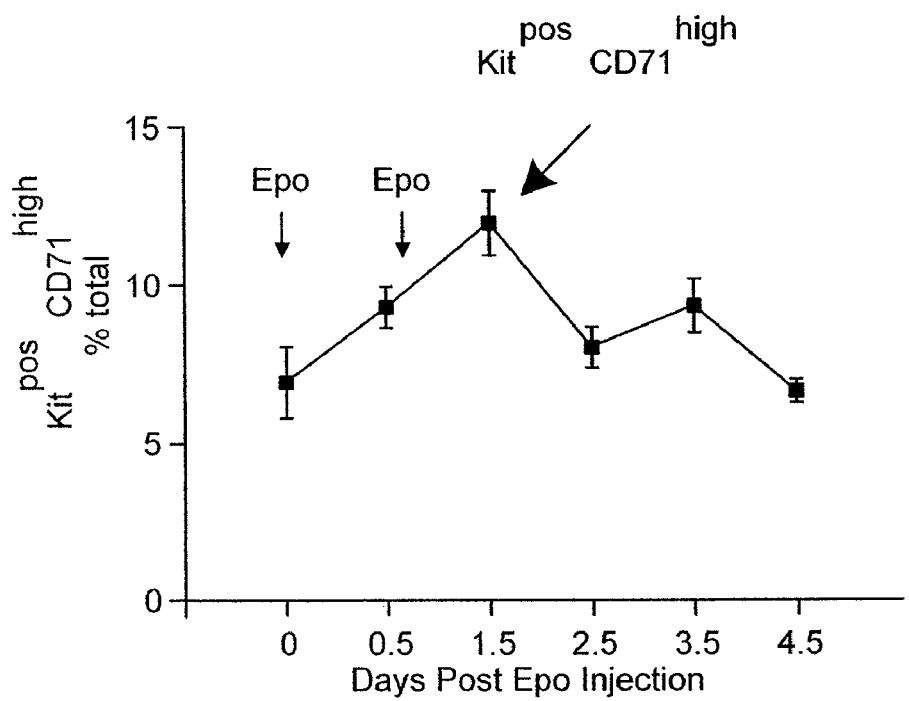
Figures 5, 5A:
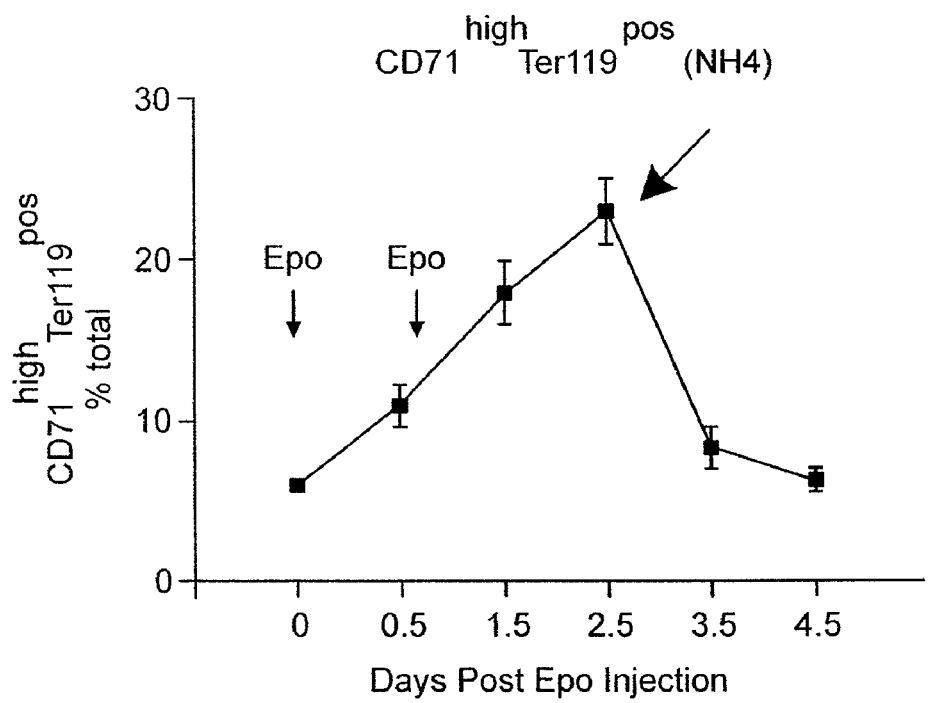
FIG. 5. Epo rapidly induces the formation of PODXL$^{pos}$ (pro)erythroblasts, and reticulocytes within bone marrow. A) Epo induction of the sequential formation of PODXL$^{pos}$ bone marrow Kit$^{pos}$CD71$^{high}$ and CD71$^{high}$ erythroblasts—Wild-type mice were injected with Epo (1500 U/mL) at 1 and 24 hours. At days 0.5, 1.5, 2.5, 3.5 and 4.5, levels of marrow resident PODXL$^{pos}$ (and total) Kit$^{pos}$CD71$^{high}$ (pro)erythroblasts, NH$_4$Cl-resistant CD71$^{high}$Ter119$^{pos}$ erythroblasts, and overall CD71$^{high}$Ter119$^{pos}$ erythroblasts were determined. For these populations, note the sequential waves of Epo-induced PODXL$^{pos}$ erythroblast formation (arrows). B) Epo-induced formation of marrow-resident R5- and R4-PODXL$^{pos}$ reticulocytes. For R4 reticulocytes, also note the rapid Epo-induced decrease of this cohort within marrow.
Figures 5, 5A, 6:
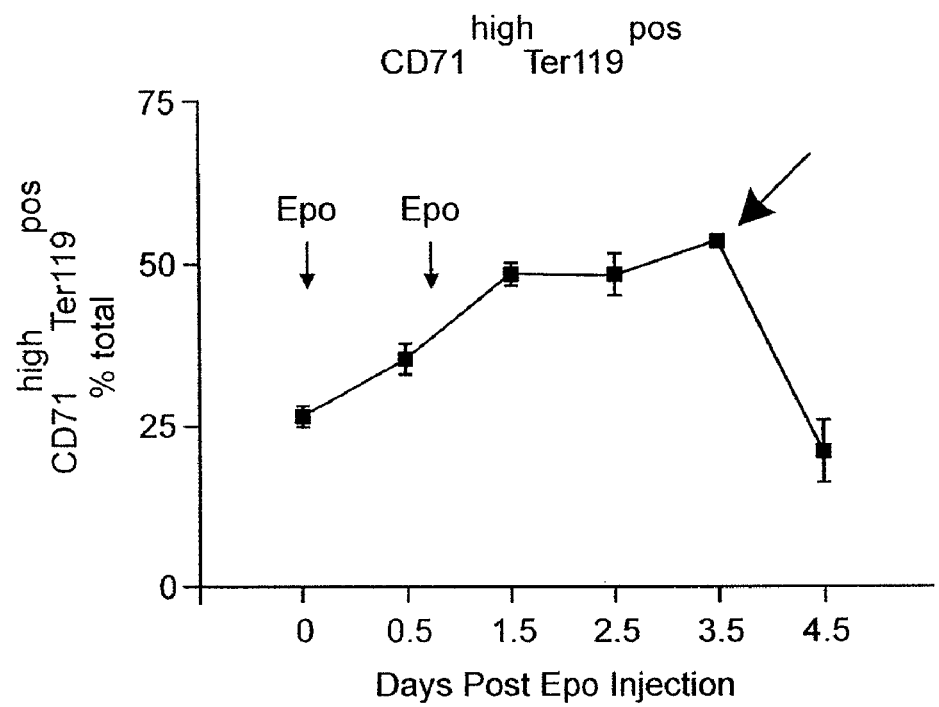
FIG. 6. Epo rapidly increases cell surface densities of PODXL expression in R5 and R4 bone marrow reticulocytes. A) In Epo-injected wild-type mice, cell surface levels (i.e. densities) of PODXL expression were assayed among bone marrow resident R5 and R4 reticulocytes. Values (relative fluorescent intensities) are means (+/−SE) for n=3 independent mice. Lower panels illustrate representative flow cytometry profiles at days 0, 0.5 and 1.5. B) R4 and R5 reticulocytes in peripheral blood also were assayed in Epo-treated mice, including total and PODXL$^{pos}$ reticulocytes populations. For R4 reticulocytes, note the rapid pulse of PODXL positivity at day 0.5 (upper right panel, arrow).

In vivo findings for $PODXL^{pos}$ expression among circulating reticulocytes prompted analyses of Epo-induced PODXL-positive erythroid progenitor cell production in marrow. Here, Epo was observed to stimulate sequential increases in the production of $PODXL^{pos}Kit^{pos}CD71^{high}$ pro-erythroblasts, $NH_4Cl$-exposed early stage $CD71^{high}Ter119^{pos}$ erythroblasts, and maturing $CD71^{high}Ter119^{pos}$ erythroblasts (FIG. 5A, right panels). For these cohorts, peak representation occurred at days 1.5, 2.5 and 3.5, respectively, and frequencies of PODXL$^{pos}$ erythroblasts (due to Epo) increased to 65%, 85% and 72% (FIG. 5A, left panels). These analyses therefore established the nature of these (pro)erythroblast populations as in vivo targets for Epo-modulation of PODXL.

Figures 1, 5B:
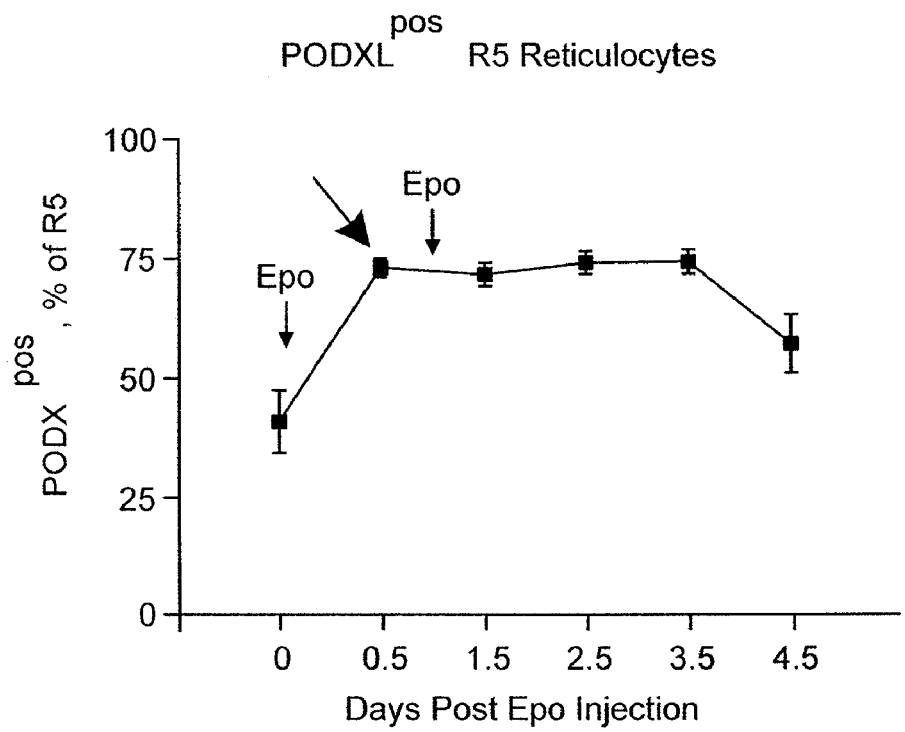
Figures 2, 5B:
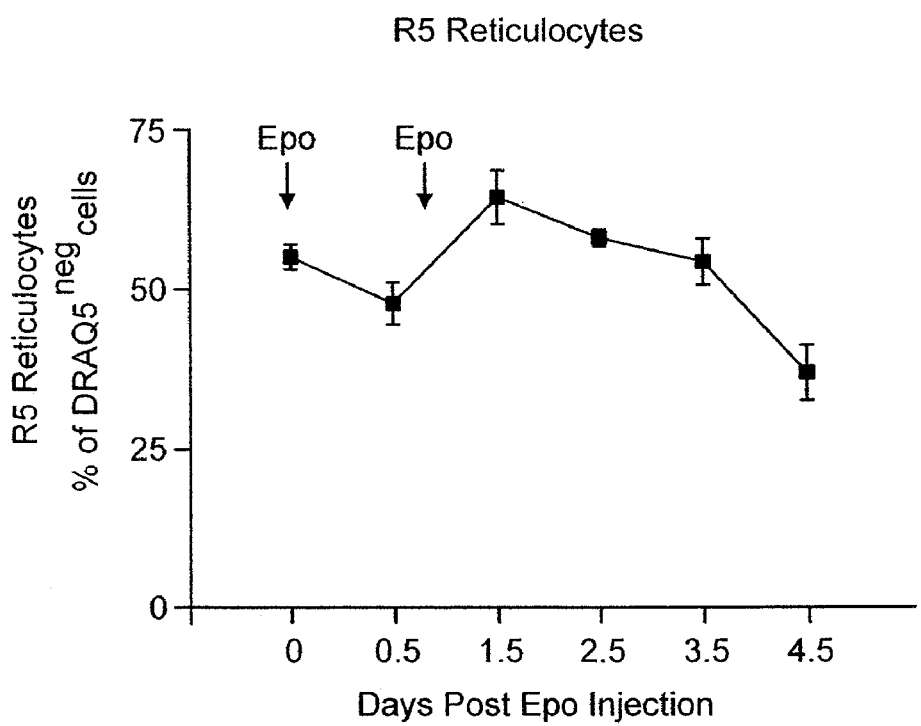
Figures 3, 5B:
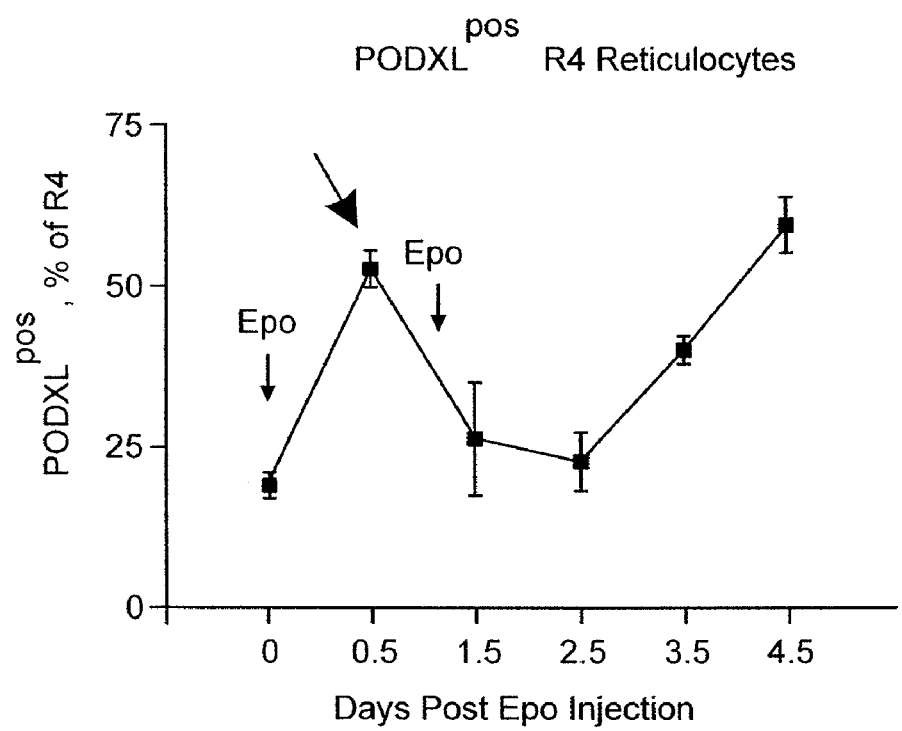
Figures 4, 5B:
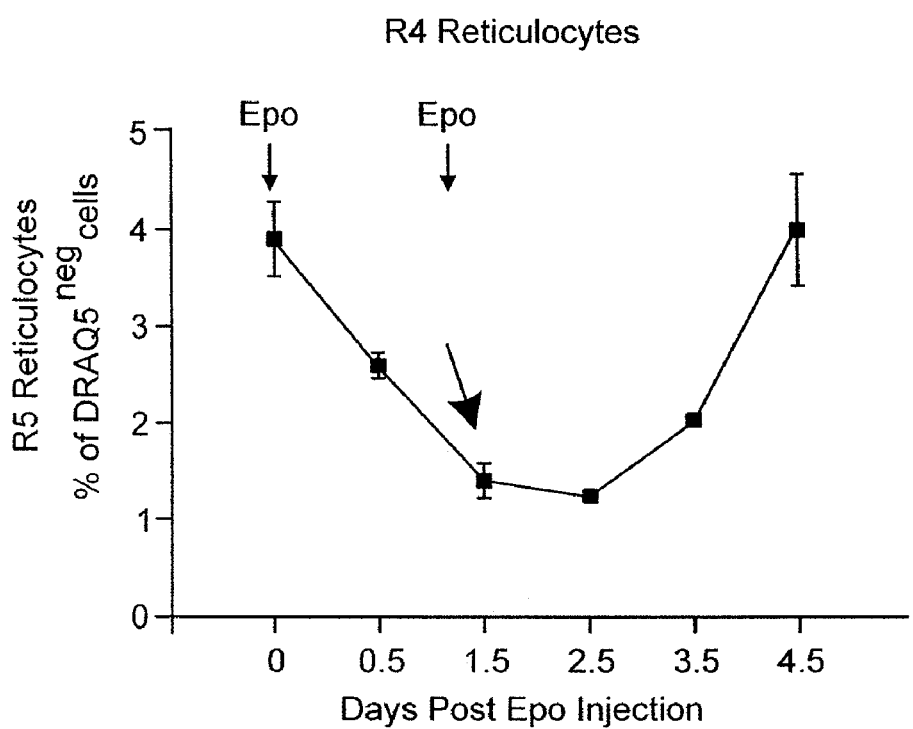
Figures 1, 6A:
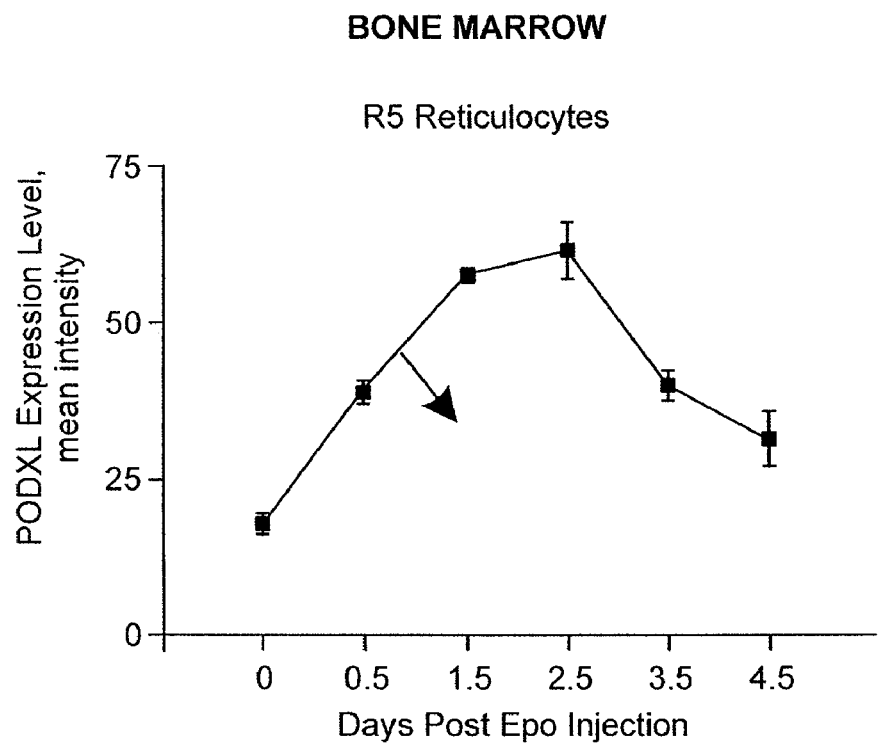
Figures 2, 6A:
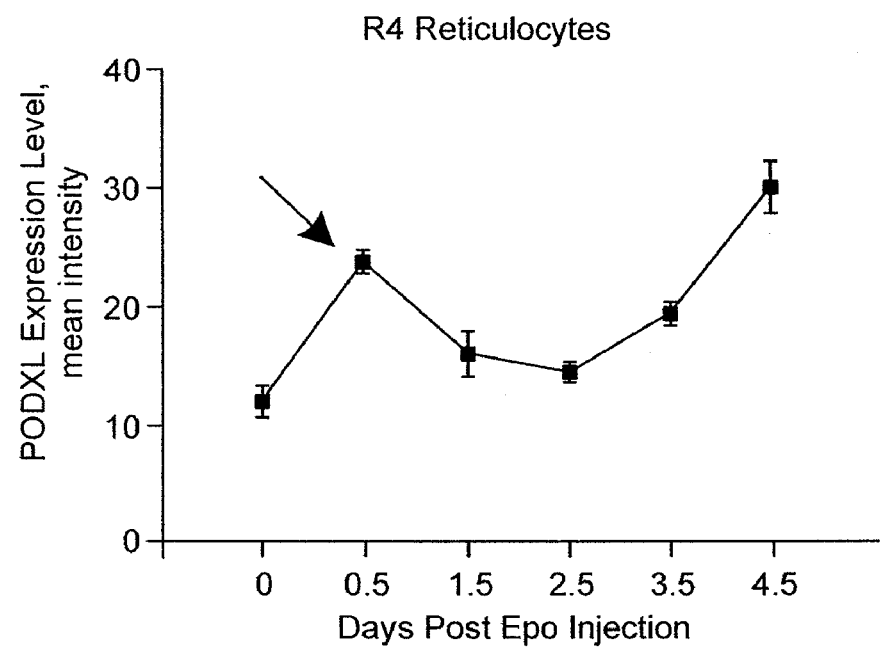
Figures 3, 6A:
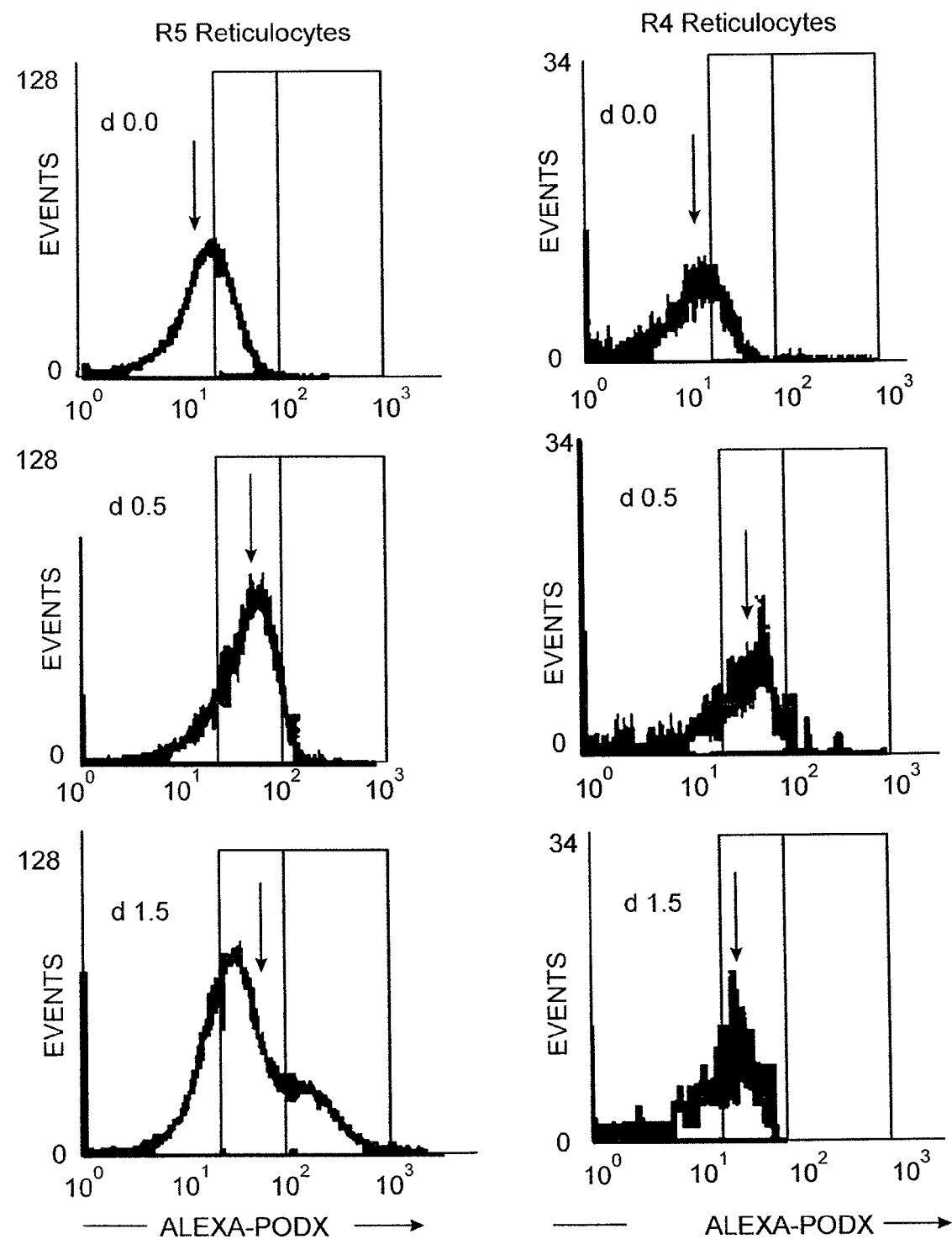
Figures 1, 6B:
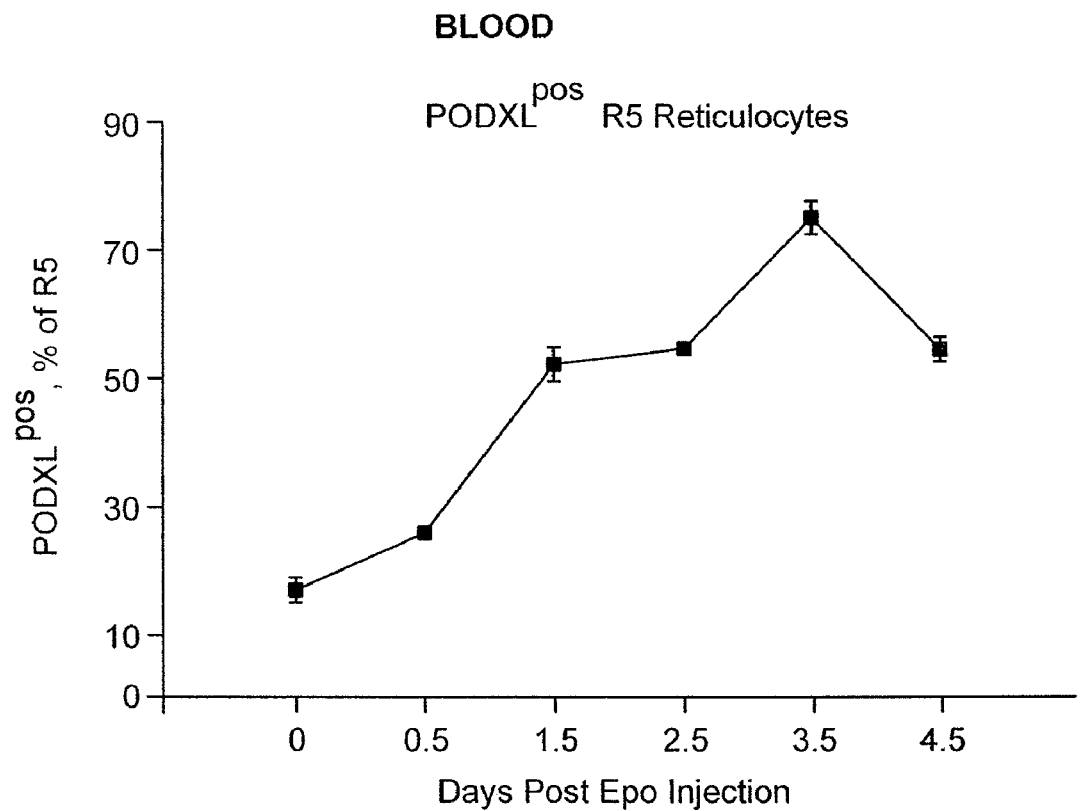
Figures 2, 6B:
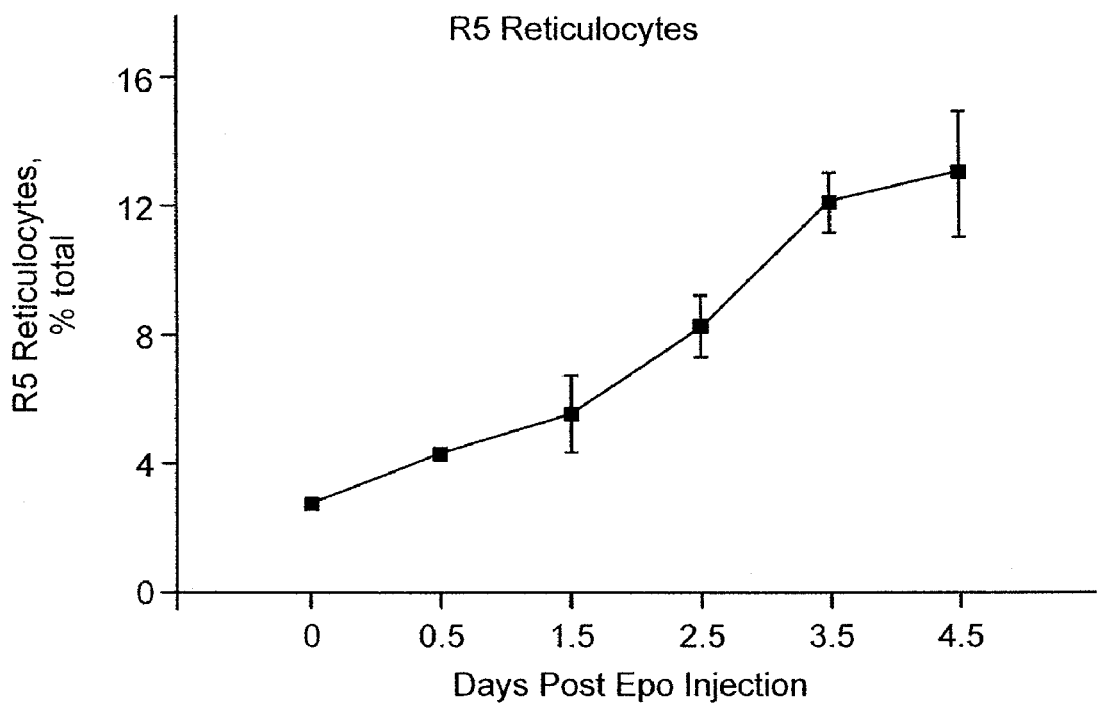
Figures 3, 6B:
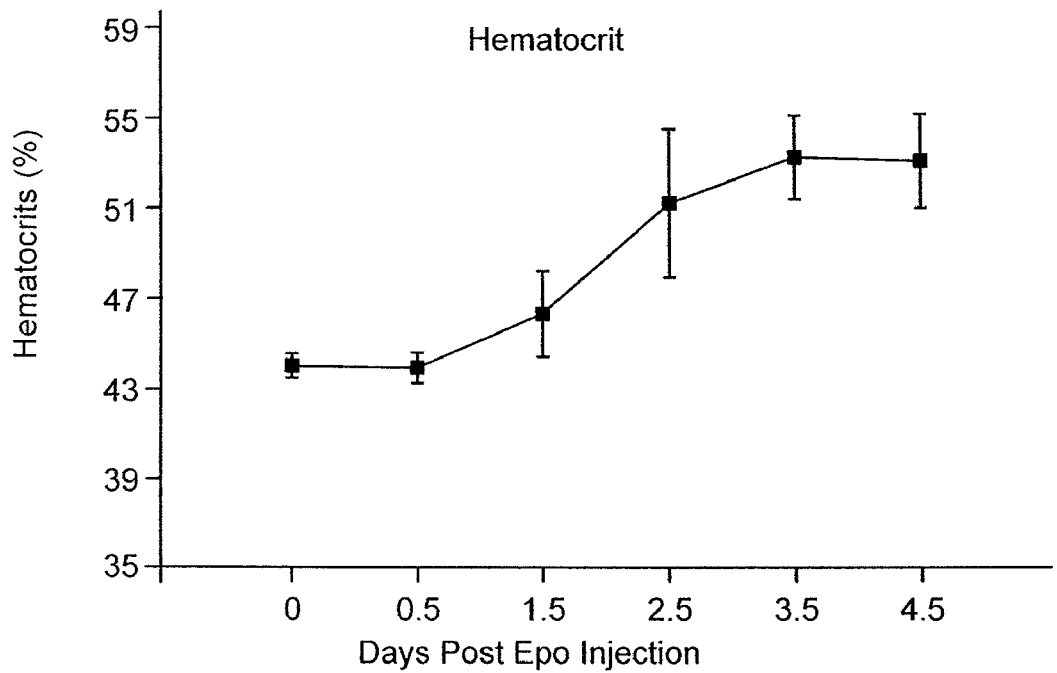
Figures 4, 6B:
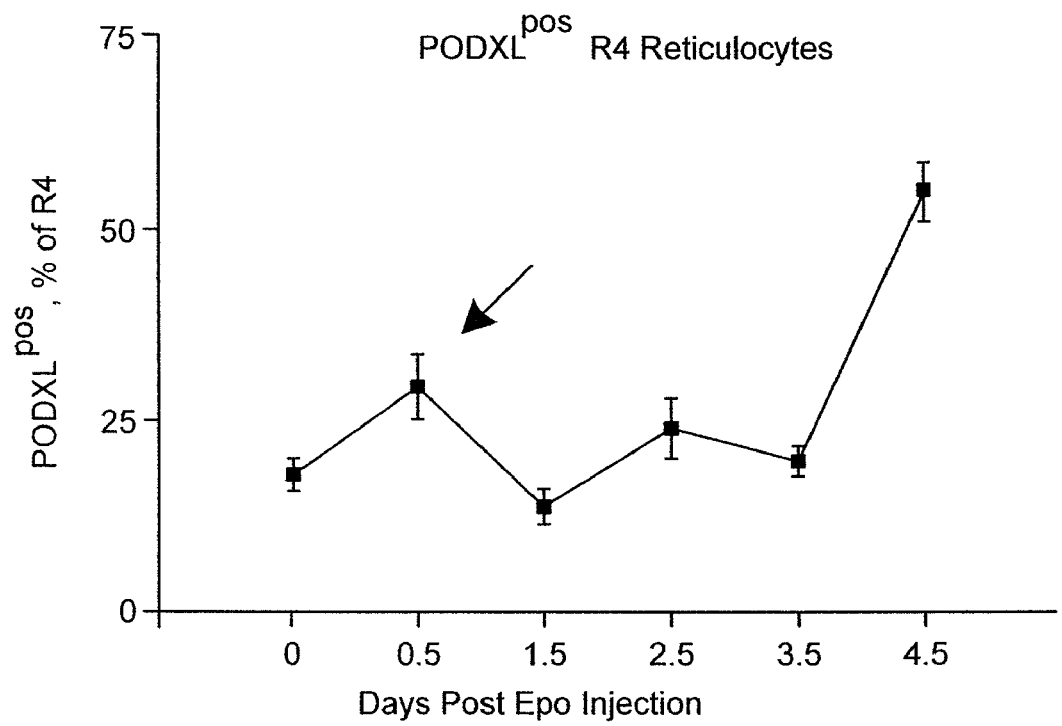
Figures 5, 6B:
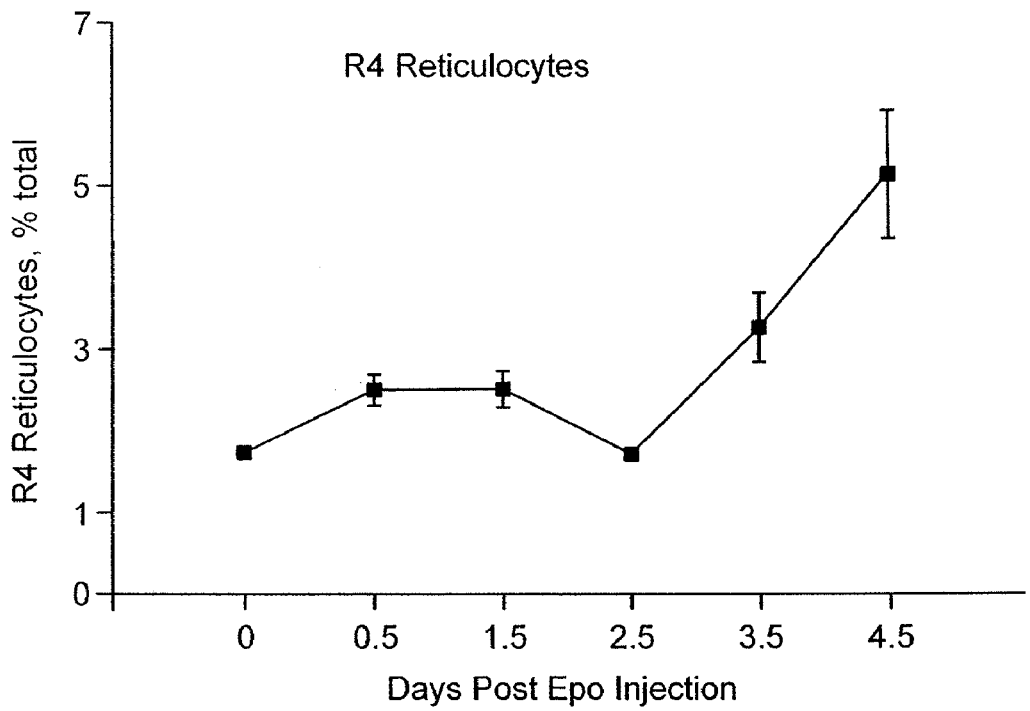
Figures 6, 6B:
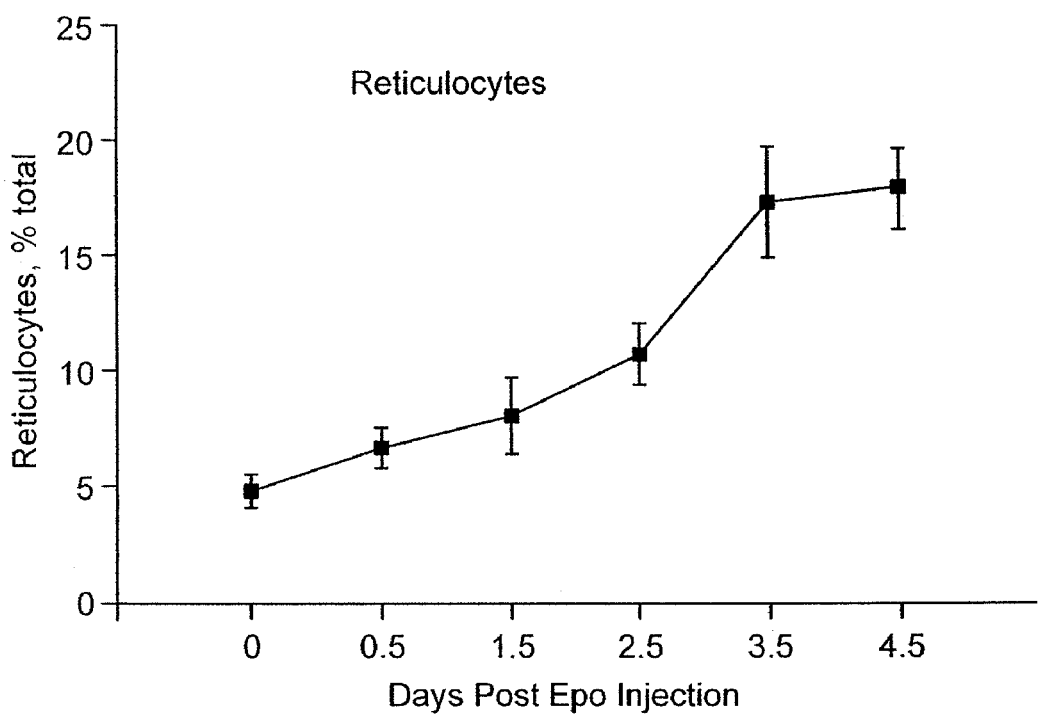

Using a combination of Draq5 staining and light scatter properties (in parallel with thiazole orange), it also was possible to assay the formation of bone marrow-resident early R5- and late R4-stage reticulocytes. In this compartment, two unexpected Epo-induced events were observed. First, in both R5 and R4 populations, frequencies of PODXL$^{pos}$ reticulocytes increased several fold within 0.5 days of Epo exposure (FIG. 5B, upper panels). Second, this was paralleled by an apparent decrease in overall numbers of marrow-resident R4 reticulocytes. This latter event is consistent with rapid Epo- (and possibly PODXL-) dependent effects on R4 reticulocyte release to blood. Epo's apparent ability to modulate PODXL expression in marrow reticulocytes was analyzed further based on levels of Epo-induced expression (as assayed via relative fluorescence intensities of PODXL staining) (FIG. 6A). In R5, and to a lesser yet significant extent in R4 reticulocytes, surface cell levels of PODXL expression were up-modulated several fold by Epo within 0.5 to 1.5 days. In parallel analyses of blood, frequencies of circulating PODXL$^{pos}$ R5 and R4 reticulocytes increased overall by ~6 fold and ~4 fold, respectively (FIG. 6B)—and this included a rapid pulse in PODXL$^{pos}$ R4 reticulocyte levels at day 0.5 (upper right panel, arrow).

Figure 7A:
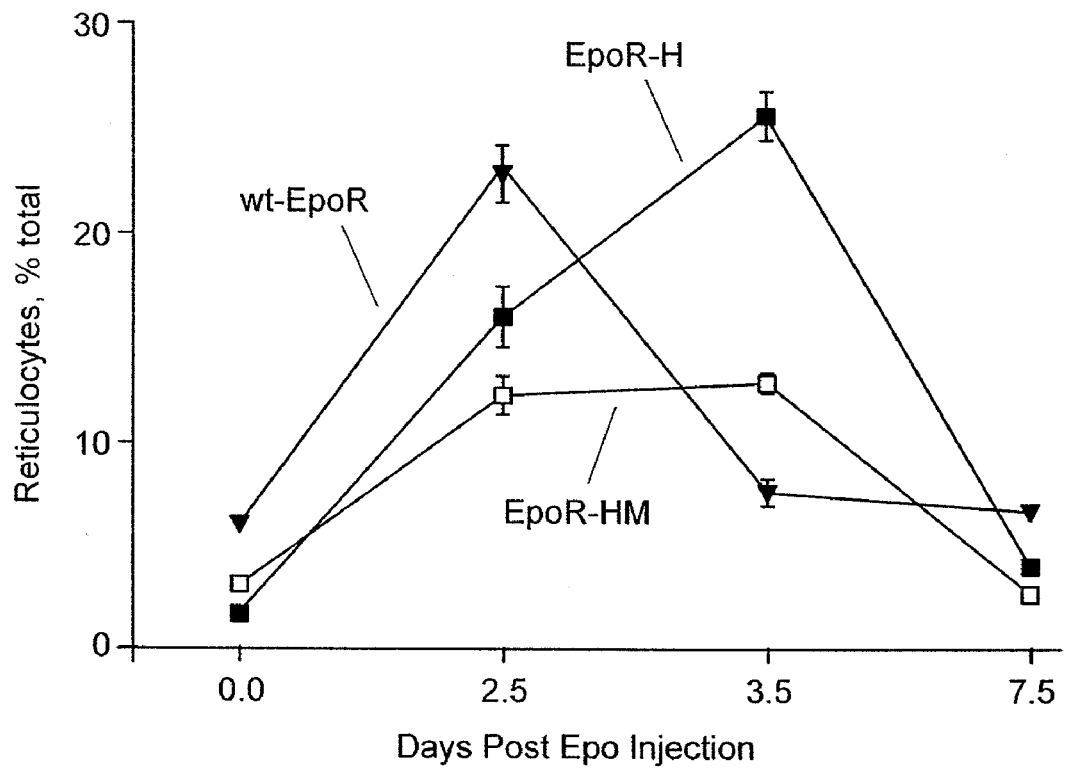
FIG. 7. EpoR-deficient HM reticulocyte production in response to Epo, and abnormal representation of anucleate red cells in EpoR-HM marrow. A] For wt-EpoR, EpoR-HM and EpoR-H mice, time courses of Epo-induced in vivo reticulocyte production are graphed (left panel) (means+/− SE, n=5 per group, 1200 U/kg). Frequencies of PODXL$^{pos}$ immature reticulocytes (IRF, day-3 post Epo) also are illustrated (right panel). B] Wild-type (wt-EpoR), EpoR-HM and EpoR-H mice were treated with Epo at 0, 1200 and 1800 U/kg. At day-3.5, Levels of PODXL expression among immature reticulocytes were determined. C] In bone marrow of wt-EpoR, EpoR-HM and EpoR-H mice (a day-3 post-Epo injection, 1500 U/kg) relative frequencies (ratios) of anucleated vs. nucleated Ter119$^{pos}$ cells were determined based on DRAQ5 staining of Ter119$^{pos}$ cells.
Figure 7A:
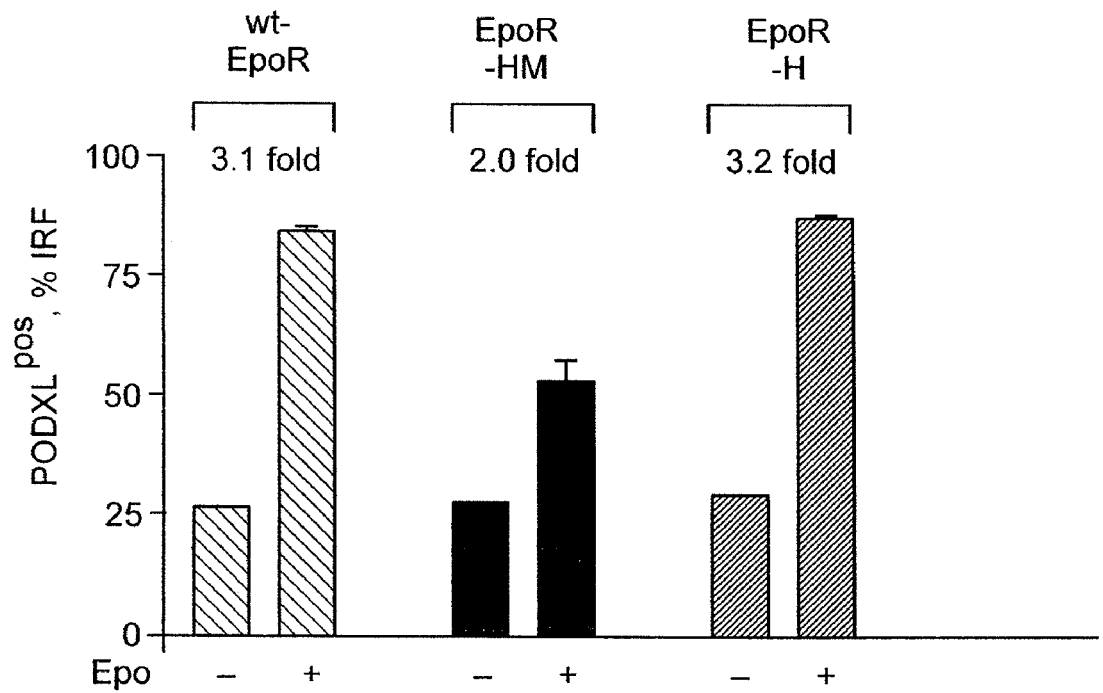
Figure 7B:
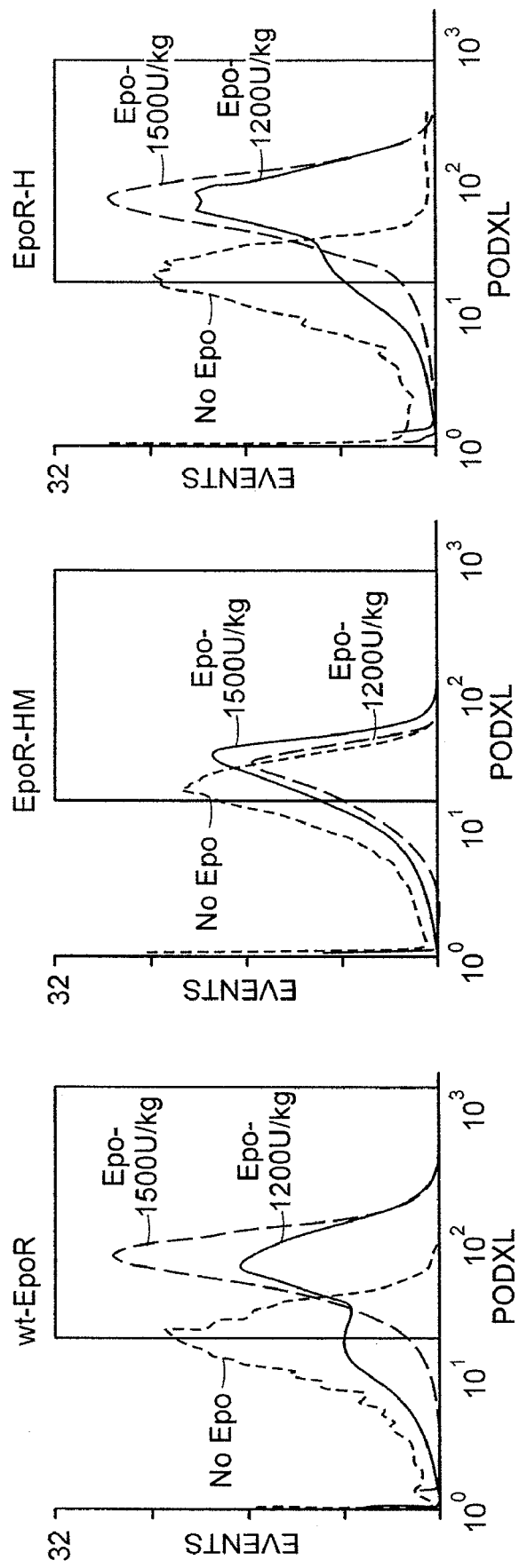
Figure 7C:
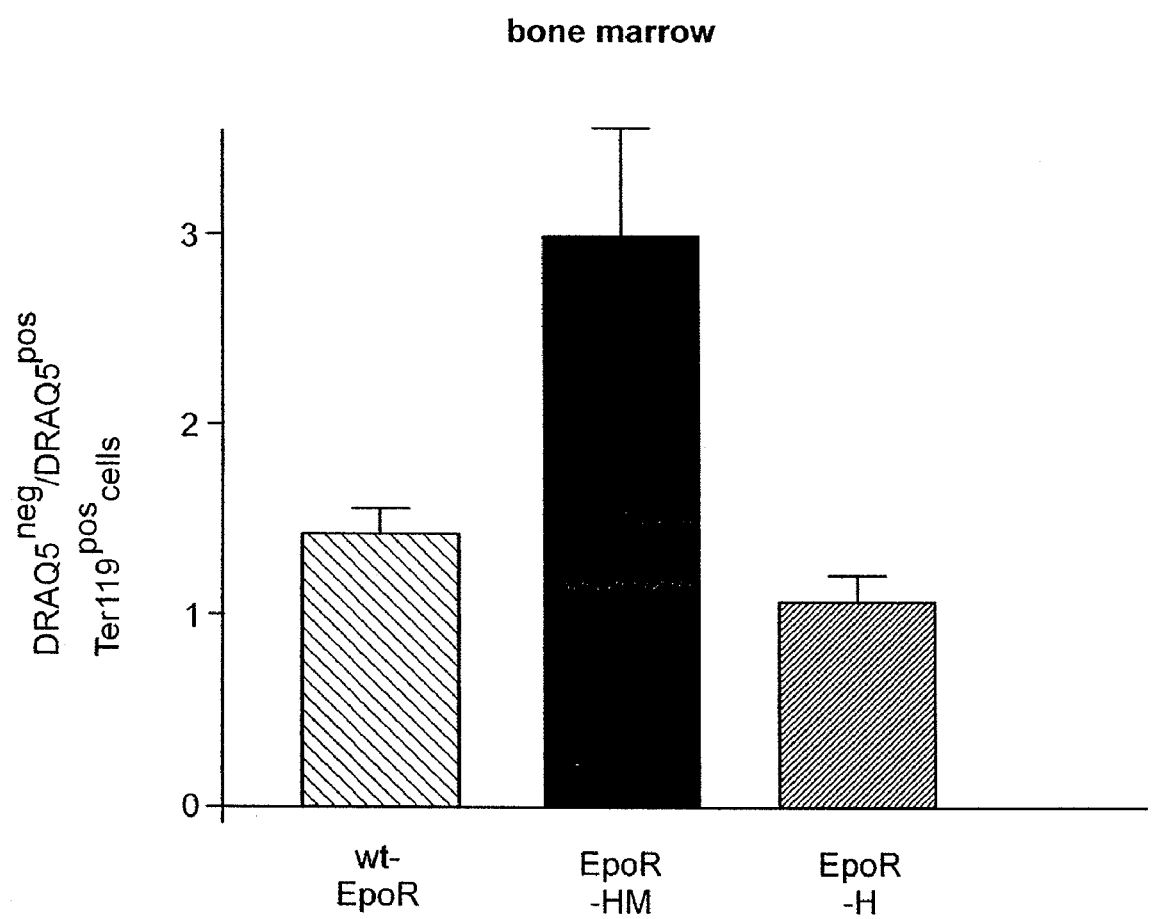

Finally, Epo-induced PODXLP$^{pos}$ erythroid cell formation was examined in wt-EpoR, EpoR-HM and EpoR-H mice. As described by Zang, et al. (The distal region and receptor tyrosines of the Epo receptor are non-essential for in vivo erythropoiesis. *Embo J* 20:3156-3166, 2001), EpoR-HM mice possess approximately wild-type BFUe CFUe levels, and generate a near normal red cell mass at steady-state. As described by Menon et al (Menon, M. P., et al., 2006. Signals for stress erythropoiesis are integrated via an erythropoietin receptor-phosphotyrosine-343-Stat5 axis. *J Clin Invest* 116: 683-694), however, this EpoR allele selectively fails to support efficient stress erythropoiesis. During Epo-induced reticulocyte formation, possible in vivo correlations with diminished PODXL expression levels in EpoR-HM mice therefore were sought. Interestingly, EpoR-HM mice failed to generate normal levels of circulating reticulocytes, even at high Epo doses (1800 U/kg)—and this paralleled a deficient representation of PODXL$^{pos}$ reticulocytes within an IRF compartment (FIG. 7A). Furthermore, EpoR-H mice exhibited clear Epo dose-dependent PODXL expression in the IRF while in EpoR-HM mice, the percentage of PODXL-expressing immature reticulocytes remained largely unchanged in response to increasing Epo doses (1200 U/kg and 1500 U/kg) (FIG. 7B). Beyond this, when frequencies of nucleated marrow-resident red cells were analyzed (via Draq5 and Ter119 co-staining), abnormally elevated levels were observed in EpoR-HM marrow (FIG. 7C). This latter finding is consistent with an aberrant retention of late-stage red cells, and correlates well with deficiencies in PODXL expression.

Figure 8:
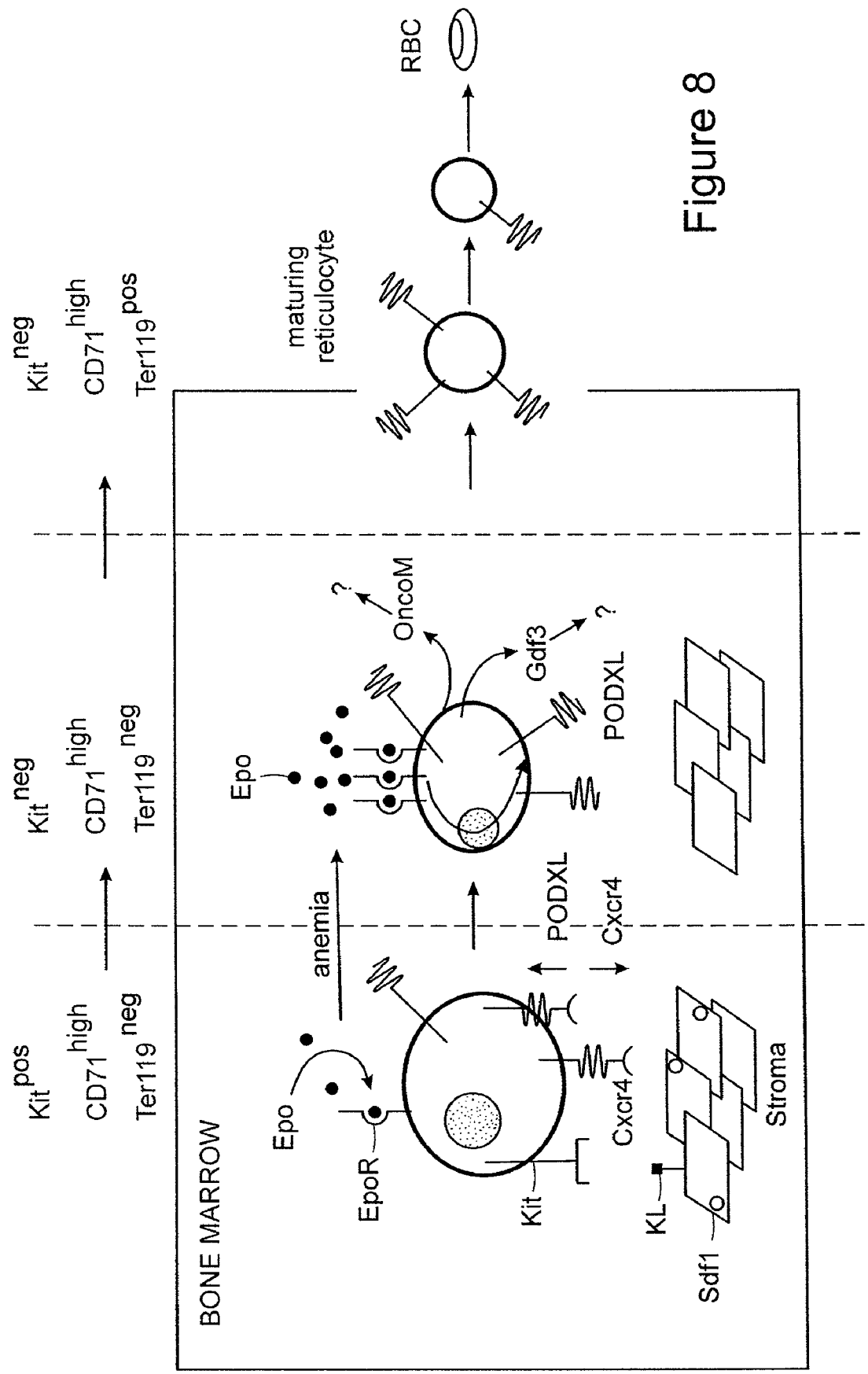
FIG. 8. Model for Epo-regulation of erythroid progenitor cell adhesion and migration within a proposed stromal niche. Epo's actions on Kit$^{pos}$CD71$^{high}$ proerythroblasts are depicted to involve an Epo dose-dependent repression of Cxcr4 expression and an induction of PODXL. This Epo response is sustained as progenitors advance to a Kit$^{neg}$CD71$^{high}$ erythroblast stage and exit a proposed stromal niche. Epo-dependent PODXL expression further persists among immature reticulocytes, and is hypothesized to enhance their release to blood.

Somewhat unexpectedly, Epo's effects on PODXL expression proved to be exerted not only in late-stage erythroblasts, but also within reticulocyte (immature red blood cell) populations thereby making the detection of PODXL up-regulation a novel method for the screening of Epo use (including Epo-derivatives and mimetics) by, for example, athletes. Because Epo is thought to act primarily on late CFUe stage erythroblasts, apparent effects in derived reticulocytes could involve, for example, a stabilization of PODXL transcripts and/or protein. Increases in PODXL expression levels in stage R4 and R5 reticulocytes were rapidly affected by Epo (i.e., within ≦12 hours). In mice expressing a minimal PY-null EpoR allele (EpoR-HM), Epo failed to efficiently stimulate circulating reticulocyte production. This result, together with discovered effects of Epo on a select set of adhesion factors (and cytokines) in bone marrow erythroblasts, supports the case that a novel action mode exists via which Epo acts dynamically (especially during anemia) to modulate (pro)erythroblast surfaces within a stromal niche and to promote their migration (possibly to blood islands) (see, model, FIG. 8).

The invention claimed is:

1. A method for detecting, in vivo, the effects of exogenous Epo or derivatives or mimetics thereof, the method comprising:
    a) providing a blood sample from an individual;
    b) determining the level of expression of an Epo responsive gene product on the surface of circulating erythroid cells in the blood sample of the individual, the Epo responsive gene product being selected from the group consisting of podocalyxin and growth differentiation factor-3;
    c) comparing the level of expression determined in step b) with a standard level of expression accepted as representative of the in vivo expression level on the surface of red blood cells in the individual in the absence of exogenous Epo or derivatives or mimetics thereof, a substantial increase in the level determined in step b), as compared with the standard level of expression accepted as representative of the in vivo expression level on the surface of red blood cells in the individual in the absence of exogenous Epo or derivatives or mimetics thereof, being indicative of the effects of exogenous Epo or derivatives or mimetics thereof.

2. The method of claim 1, wherein the Epo-responsive gene product is podocalyxin.

3. The method of claim 1, wherein said Epo-responsive gene product is detected by an immunological technique.

4. The method of claim 3, wherein said immunological technique is an assay selected from a group consisting of fluorescent labeling, flow cytometry, Western blot, immunosandwich assay and immunodiffusion assay.

5. The method of claim 1, wherein said Epo-responsive gene product is detected by PCR, Northern blot or Southern blot or a combination thereof.

6. The method of claim 1, wherein said circulating erythroid cells are selected from one or more of reticulocytes, erythroblasts and red blood cells.

7. The method of claim 1, wherein said exogenous Epo, Epo-derivatives and mimetics are selected from a group consisting of Aransep, Epo-PEG conjugates, recombinant Epo and Epo mimetics.

8. The method of claim 1, wherein said EPO responsive gene product is, growth differentiation factor-3.

* * * * *